(12) United States Patent
Harada et al.

(10) Patent No.: US 11,066,477 B2
(45) Date of Patent: Jul. 20, 2021

(54) MONOCLONAL ANTIBODY AGAINST MELK AND UTILIZATION THEREOF

(71) Applicant: ONCOTHERAPY SCIENCE, INC., Kawasaki (JP)

(72) Inventors: Yosuke Harada, Kawasaki (JP); Suyoun Chung, Kawasaki (JP); Yusuke Nakamura, Kawasaki (JP)

(73) Assignee: ONCOTHERAPY SCIENCE, INC., Kawasaki (JP)

(*) Notice: Subject to any disclaimer, the term of this patent is extended or adjusted under 35 U.S.C. 154(b) by 191 days.

(21) Appl. No.: 16/328,259

(22) PCT Filed: Aug. 25, 2017

(86) PCT No.: PCT/JP2017/030443
§ 371 (c)(1),
(2) Date: Feb. 25, 2019

(87) PCT Pub. No.: WO2018/043311
PCT Pub. Date: Mar. 8, 2018

(65) Prior Publication Data
US 2019/0185575 A1    Jun. 20, 2019

(30) Foreign Application Priority Data
Aug. 31, 2016    (JP) .............................. JP2016-169085

(51) Int. Cl.
| | |
|---|---|
| *A61K 39/00* | (2006.01) |
| *C07K 16/30* | (2006.01) |
| *G01N 33/573* | (2006.01) |
| *G01N 33/574* | (2006.01) |
| *C07K 16/18* | (2006.01) |
| *C12N 15/85* | (2006.01) |

(52) U.S. Cl.
CPC .......... *C07K 16/30* (2013.01); *A61K 39/0011* (2013.01); *C07K 16/18* (2013.01); *C12N 15/85* (2013.01); *G01N 33/573* (2013.01); *G01N 33/57492* (2013.01); *A61K 39/00118* (2018.08); *A61K 39/001154* (2018.08); *C12N 2015/8518* (2013.01); *G01N 2800/364* (2013.01); *G01N 2800/50* (2013.01); *G01N 2800/52* (2013.01)

(58) Field of Classification Search
CPC ........ C07K 16/30; C07K 16/18; C07K 16/40; A61K 39/0011; A61K 39/00118; C12N 15/85; G01N 33/573
See application file for complete search history.

(56) References Cited

U.S. PATENT DOCUMENTS

| | | |
|---|---|---|
| 2006/0024692 A1 | 2/2006 | Nakamura et al. |
| 2009/0175844 A1 | 7/2009 | Nakamura et al. |
| 2009/0263395 A1 | 10/2009 | Nakamura et al. |
| 2009/0317392 A1 | 12/2009 | Nakamura et al. |
| 2011/0152106 A1 | 6/2011 | Lee et al. |
| 2011/0212115 A1 | 9/2011 | Tsunoda et al. |
| 2012/0014996 A1 | 1/2012 | Nakamura et al. |
| 2013/0011933 A1 | 1/2013 | Nakamura et al. |
| 2013/0034574 A1 | 2/2013 | Nakamura et al. |
| 2014/0141028 A1 | 5/2014 | Tsunoda et al. |
| 2015/0353935 A1 | 12/2015 | Huang et al. |
| 2016/0101171 A1 | 4/2016 | Tsunoda et al. |

FOREIGN PATENT DOCUMENTS

| | | |
|---|---|---|
| EP | 2574929 A1 | 4/2013 |
| EP | 3239295 A | 1/2017 |
| JP | 2007-502115 A | 2/2007 |
| JP | 2010/013485 A | 2/2010 |
| JP | 2013-517764 A | 5/2013 |
| RU | 2504785 C1 | 1/2014 |
| WO | 2004/031413 A | 4/2004 |
| WO | 2005/016279 A | 2/2005 |
| WO | 2005/073374 A | 8/2005 |
| WO | 2006/016525 A | 2/2006 |
| WO | 2006/085684 A | 8/2006 |
| WO | 2007/013665 A | 2/2007 |
| WO | 2007/058933 A | 5/2007 |
| WO | 2008/023841 A | 2/2008 |
| WO | 2011/089921 A | 7/2011 |
| WO | 2012/016082 A | 2/2012 |
| WO | 2013/109388 A | 7/2013 |
| WO | 2016/092865 A | 6/2016 |

OTHER PUBLICATIONS

Paul, Fundamental Immunology, 3rd Edition, 1993, pp. 292-295 (Year: 1993).*
Rudikoff et al(Proc. Natl. Acad. Sci. USA 1982 vol. 79: p. 1979). (Year: 1982).*
Pascalis et al (The Journal of Immunology (2002) 169, 3076-3084) (Year: 2002).*
Casset et al. (2003) BBRC 307, 198-205 (Year: 2003).*
George et al. (Circulation. 1998; 97: 900-906), (Year: 1998).*
Blot, et al; Cell Cycle Regulation of pEg3, a New Xenopus Protein Kinase of the KIN1/PAR-1/MARK Family; Dev. Bio. Jan. 15, 2002:241(2):327-38.

(Continued)

*Primary Examiner* — Sheela J. Huff
(74) *Attorney, Agent, or Firm* — Kilpatrick Townsend & Stockton LLP

(57) ABSTRACT

The present invention relates to monoclonal antibodies against MELK. Furthermore, the present invention provides methods for diagnosing MELK-associated diseases using the antibodies, methods for detecting the MELK protein, methods for determining the drug efficacy following treatment with a MELK inhibitor, methods of screening for subjects to whom a MELK inhibitor has a high therapeutic effect, and diagnostic reagents containing the antibodies.

10 Claims, 6 Drawing Sheets

Specification includes a Sequence Listing.

(56) References Cited

OTHER PUBLICATIONS

Chung, et al; Development of an orally-administrative MELK-targeting inhibitor that suppresses the growth of various types of human cancer; Oncotarget; Dec. 2012; 3(12):1629-40.

Chung, et al; Preclinical evaluation of biomarkers associated with antitumor activity of MELK inhibitor; Oncotarget; Apr. 5, 2016; 7(14):18171-82.

Heyer, et al; Expression of MELK, a New Protein Kinase, During Early Mouse Development; Dev Dyn.; Aug. 1999; 215(4):344-51.

Inoue, et al; Effective growth-suppressive activity of maternal embryonic leucine-zipper kinase (MELK) inhibitor against small cell lung cancer; Oncotarget; Mar. 22, 2016; 7(12):13621-33.

Lin, et al; Involvement of maternal embryonic leucine zipper kinase (MELK) in mammary carcinogenesis through interaction with Bcl-G, a pro-apoptotic member of the Bcl-2 family; Breast Cancer Res.; 2007; 9(1):R17.

Matsuda, et al; p53-independent p21 induction by MELK inhibition; Oncotarget; Jun. 15, 2017:8(35):57938-57947.

Nakano, et al; Maternal embryonic leucine zipper kinase (MELK) regulates multipotent neural progenitor proliferation; J Cell Biol. Aug. 1, 2005;170(3):413-27.

Seong, et al; Phosphorylation of a novel zinc-finger-like protein, ZPR9, by murine protein serine/threonine kinase 38 (MPK38); Biochem J.; Feb. 1, 2002;361(Pt3):597-604.

Stefka, et al; Anti-myeloma activity of MELK inhibitor OTS167: effects on drug-resistant myeloma cells and putative myeloma stem cell replenishment of malignant plasma cells; Blood Cancer J.; Aug. 19, 2016;6(8):e460.

Vulsteke, et al; Inhibition of Spliceosome Assembly by the Cell Cycle-regulated Protein Kinase MELK and Involvement of Splicing Factor NIPP1; J. Biol. Chem.; Mar. 5, 2004; 279(10):8642-7.

Japan Patent Office; International Search Report; PCT/JP2017/030443; dated Nov. 21, 2017.

Anonymous; HPA017214 Anti-MELK antibody produced in rabbit; Jan. 1, 2020; www.sigmaaldrich.com; pp. 1-4.

European Patent Office; Supplementary European Search Report; dated Mar. 12, 2020; EP Application No. 17 84 6316; 2 pgs.

Mariuzza, et al; The Structural Basis of Antigen-Antibody Recognition; Ann. Rev. Biophys. Biophys. Chem.; 1987; 16:139-59.

Roitt, et al; Enzymatic degradation of human IgG1; Moscow "Mir"; 2000; 6 pgs.

Singer, et al; Genes and Genomes; University Science Books; Jan. 1991; 6 pgs.

* cited by examiner

MONOCLONAL ANTIBODY AGAINST MELK AND UTILIZATION THEREOF

CROSS-REFERENCE TO RELATED APPLICATIONS

The present application is a § 371 National Phase Application of PCT/JP2017/030443, filed Aug. 25, 2017, which application claims the benefit of Japanese Patent Application No. JP 2016-169085, filed Aug. 31, 2016, the entire contents of which are incorporated by reference in their entireties for all purposes herein.

TECHNICAL FIELD

The present invention relates to monoclonal antibodies against MELK, methods for diagnosing MELK-associated diseases using said antibodies, methods for detecting MELK protein, methods for determining drug efficacy following treatment with a MELK inhibitor, methods of screening for subjects to whom a MELK inhibitor has a high therapeutic effect, and diagnostic reagents comprising said antibodies.

BACKGROUND ART

MELK, namely Maternal Embryonic Leucine zipper Kinase (reference sequence: GenBank Accession No: NM_014791.3; SEQ ID NO: 21) was identified sometime back as a new member of the serine-threonine kinase family snf1/AMPK that is involved in mammalian embryonic development (Heyer BS et al., Dev Dyn. 1999 Aug., 215(4): 344-51 (NPL 1). Ibis gene has been shown to play an important role in regeneration of stem cells (Nakano I et al., J. Cell Biol. 2005 Aug. 1, 170(3): 413-27 (NPL 2)), cell cycle progression (Blot J et al., Dev Biol. 2002 Jan. 15, 241(2): 327-38 (NPL 3); Seong HA et al., Biochem J. 2002 Feb. 1, 361(Pt 3): 597-604 (NPL 4)), and mRNA precursor splicing (Vulsteke V et al., J. Biol Chem. 2004 Mar. 5, 279(10): 8642-7. Epub 2003 Dec. 29 (NPL 5)).

In addition, gene expression profiling using cDNA microarrays for the entire genome including 23,040 genes has shown that MELK is upregulated in breast cancer (Lin ML et al., Breast Cancer Res. 2007, 9 (1): R17 (NPL 6); WO 2006/016525 (PTL 1); and WO 2008/023841 (PTL 2)). In fact, MELK is upregulated in several cancer cells, for example, in lung cancer cells, bladder cancer cells, lymphoma cells, cervical cancer cells, and such (see WO 2004/031413 (PTL 3); WO 2007/013665 (PTL 4); and WO 2006/085684 (PTL 5)). Northern blot analysis of multiple human tissues and cancer cell lines has proven that although MELK is overexpressed at a significantly high level in a majority of breast cancers and breast cancer cell lines, it is not expressed in normal vital organs (heart, liver, lung and kidney) (WO 2006/016525 (PTL 1)). Moreover, it has been shown that suppression of MELK expression by siRNA leads to significant inhibition of the proliferation of human breast cancer cells (PTL 1), and that a small-molecule inhibitor against MELK reduces the size of a mouse breast cancer xenograft (Chung S et al., Oncotarget. 2012 Dec., 3(12): 1629-1640 (NPL 7); Chung S et al., Oncotarget. 2016 Feb. 24, 7(14): 18171-18182 (NPL 8)).

Therefore, MELK is thought to be a suitable target for anti-cancer agents, and a monoclonal antibody against MELK can be predicted to be useful as a diagnostic agent in therapy. In addition to examples of successful monoclonal antibody clinical applications like Trastuzumab diagnostic agent, Rituximab diagnostic agent, and Bevacizumab diagnostic agent against breast cancer, malignant lymphoma, and colon cancer, several monoclonal antibodies against other molecular targets are being developed, and their diagnostic effects evaluated. From the viewpoint of effective patient selection for therapeutic agents, these diagnostic agents are anticipated to lead to more effective methods of treatment.

CITATION LIST

Patent Literatures

[PTL 1] WO 2006/016525
[PTL 2] WO 2008/023841
[PTL 3] WO 2004/031413
[PTL 4] WO 2007/013665
[PTL 5] WO 2006/085684

Non-Patent Literatures

[NPL 1] Heyer BS et al., Dev Dyn. 1999 Aug., 215(4): 344-51
[NPL 2] Nakano I et al., J. Cell Biol. 2005 Aug. 1, 170(3): 413-27
[NPL 3] Blot J et al., Dev Biol. 2002 Jan. 15, 241(2): 327-38
[NPL 4] Seong HA et al., Biochem J. 2002 Feb. 1, 361(Pt 3): 597-604
[NPL 5] Vulsteke V et al., J. Biol Chem. 2004 Mar. 5, 279(10): 8642-7. Epub 2003 Dec. 29
[NPL 6] Lin ML et al., Breast Cancer Res. 2007, 9(1): R17
[NPL 7] Chung S et al., Oncotarget. 2012 Dec., 3(12): 1629-1640
[NPL 8] Chung S et al., Oncotarget. 2016 Feb. 24, 7(14): 18171-18182

DISCLOSURE OF THE INVENTION

Problems to be Solved by the Invention

It is important for diagnostic agents in the treatment of tumor that use molecularly-targeted drugs to detect cellular proteins that are overexpressed in most parts of a target tumor, and are either not expressed or expressed only to a minimal extent in normal tissues. However, it is difficult to detect proteins expressed in tumors specifically and with a high sensitivity, and it is also hard to obtain antibodies against such proteins. For instance, regarding MELK that is considered to be a target for anti-cancer agents, there are a few antibodies on the market. However, when the present inventors stained MELK-expressing cells using commercially-available antibodies they obtained, a positive signal (false positive) was occasionally seen even in cells in which MELK expression level was low. With such antibodies having inadequate immunological specificity, there is a worry of not being able to clearly detect differences in MELK expression levels using antibody reaction strength as an indicator. Therefore, a problem to be solved by the present invention is to provide antibodies that bind to MELK specifically and with a high sensitivity.

Means for Solving the Problems

The present inventors searched for an antibody that specifically binds to MELK from among monoclonal antibodies obtained by immunizing mice with MELK antigen, and succeeded in identifying a clone that can specifically bind to the MELK protein forcedly expressed in cells, and can specifically detect endogenous MELK protein expressed within cells and tissues, with a good sensitivity.

Specifically, the present invention relates to the following:

[1] an antibody or antigen-binding fragment thereof, which can bind to MELK protein or a partial peptide thereof, and which comprises either one or both of:
   a heavy chain variable region comprising:
      a CDR1 comprising the amino acid sequence of SEQ ID NO: 1;
      a CDR2 comprising the amino acid sequence of SEQ ID NO: 2; and
      a CDR3 comprising the amino acid sequence of SEQ ID NO: 3, and
   a light chain variable region comprising:
      a CDR1 comprising the amino acid sequence of SEQ ID NO: 4;
      a CDR2 comprising the amino acid sequence of SEQ ID NO: 5; and
      a CDR3 comprising the amino acid sequence of SEQ ID NO: 6;

[2] the antibody or antigen-binding fragment thereof of [1], comprising either one or both of a heavy chain variable region comprising the amino acid sequence of SEQ ID NO: 7 and a light chain variable region comprising the amino acid sequence of SEQ ID NO: 8;

[3] the antibody or antigen-binding fragment thereof of [1] or [2], which specifically recognizes the polypeptide consisting of the amino acid sequence of SEQ ID NO: 9;

[4] an antibody or antigen-binding fragment thereof, which competes with the antibody of any one of [1] to [3] for specific binding towards MELK;

[5] the antibody or antigen-binding fragment thereof of any one of [1] to [4], which is conjugated with an affinity label, enzyme label, radioisotope label, or fluorescent label;

[6] a polynucleotide encoding the antibody or antigen-binding fragment thereof of any one of [1] to [5];

[7] a reagent comprising the antibody or antigen-binding fragment thereof of any one of [1] to [5], wherein the reagent is for diagnosing a MELK-associated disease, for determining drug efficacy following treatment with a MELK inhibitor, or for screening for a subject to whom a MELK inhibitor has a high therapeutic effect;

[8] a method for diagnosing a MELK-associated disease or a predisposition for developing said disease in a subject, comprising the steps of:
   (a) contacting a sample isolated from said subject with the antibody or antigen-binding fragment thereof of any one of [1] to [5];
   (b) detecting MELK protein in said sample by detecting the binding of said sample with said antibody or antigen-binding fragment thereof; and
   (c) comparing the MELK protein level in said sample with a control, wherein it is indicated that said subject suffers from or is at a risk of developing said disease, when the MELK protein level is high compared to the control;

[9] the reagent of [7] or the method of [8], wherein said MELK-associated disease is a cancer in which MELK is expressed or endometriosis;

[10] the reagent or method of [9], wherein said cancer is selected from the group consisting of breast cancer, bladder cancer, cervical cancer, cholangiocellular cancer, chronic myelocytic leukemia (CML), colorectal cancer, esophageal cancer, stomach cancer, liver cancer, non-small cell lung cancer (NSCLC), lymphoma, osteosarcoma, ovarian cancer, pancreatic cancer, prostate cancer, kidney cancer, and small cell lung cancer (SCLC);

[11] a method for detecting MELK protein in a sample, comprising the steps of:
   (a) contacting a sample isolated from a subject with the antibody or antigen-binding fragment thereof of any one of [1] to [5]; and
   (b) detecting MELK protein in said sample by detecting the binding of said sample with said antibody or antigen-binding fragment thereof;

[12] a method for determining drug efficacy following treatment with a MELK inhibitor in a subject, comprising the steps of:
   (a) contacting a sample isolated from a subject with the antibody or antigen-binding fragment thereof of any one of [1] to [5];
   (b) detecting MELK protein in said sample by detecting the binding of said sample with said antibody or antigen-binding fragment thereof; and
   (c) comparing the MELK protein level in said sample with the expression level before drug administration, wherein when said MELK protein level is low as compared to before drug administration, it is indicated that there was drug efficacy in said subject;

[13] a method of screening for a subject to whom a MELK inhibitor has a high therapeutic effect, comprising the steps of:
   (a) contacting a sample isolated from said subject with the antibody or antigen-binding fragment thereof of any one of [1] to [5];
   (b) detecting MELK protein in said sample by detecting the binding of said sample with said antibody or antigen-binding fragment; and
   (c) comparing the MELK protein level in said sample with a control, wherein when the MELK protein level is comparable with or higher than the control, it is indicated that the therapeutic effect by the MELK inhibitor is high in said subject;

[14] the method of any one of [8] to [13], wherein said sample is a cell or tissue isolated from said subject; and

[15] a method for producing an antibody that can bind to MELK protein, or to a partial peptide thereof, comprising the steps of:
   (a) culturing a cell comprising a vector inserted with the polynucleotide of [6]; and
   (b) recovering said antibody from the cell culture or culture medium.

The present invention further relates to:

[16] a method for detecting a marker for diagnosing a MELK-associated disease, or a predisposition for developing said disease, comprising the steps of:
   (a) contacting a sample isolated from a subject with the antibody or antigen-binding fragment thereof of any one of [1] to [5]; and
   (b) detecting MELK protein in said sample as said marker by detecting the binding of said antibody or antigen-binding fragment thereof with said sample;

[17] the antibody or antigen-binding fragment thereof of any one of [1] to [5] for use in the diagnosis of a MELK-associated disease, or a predisposition for developing said disease;

[18] use of the antibody or antigen-binding fragment thereof of any one of [1] to [5] in the manufacture of a reagent for diagnosing a MELK-associated disease, or a predisposition for developing said disease;

[19] a method for detecting a drug efficacy marker of a MELK inhibitor, comprising the steps of:
  (a) contacting a sample isolated from a subject with the antibody or antigen-binding fragment thereof of any one of [1] to [5]; and
  (b) detecting MELK protein in said sample as said marker by detecting binding of said antibody or antigen-binding fragment thereof with said sample;

[20] the antibody or antigen-binding fragment thereof of any one of [1] to [5] for use in determination of drug efficacy following treatment with a MELK inhibitor;

[21] use of the antibody or antigen-binding fragment thereof of any one of [1] to [5] in the manufacture of a reagent for determining drug efficacy following treatment with a MELK inhibitor;

[22] a method for detecting a MELK inhibitor treatment responsiveness marker, comprising the steps of:
  (a) contacting a sample isolated from a subject with the antibody or antigen-binding fragment thereof of any one of [1] to [5]; and
  (b) detecting MELK protein in said sample as said marker by detecting the binding of said antibody or antigen-binding fragment thereof with said sample;

[23] the antibody or antigen-binding fragment thereof of any one of [1] to [5] for use in screening for a subject to whom a MELK inhibitor has a high therapeutic effect; and

[24] use of the antibody or antigen-binding fragment thereof of any one of [1] to [5] in the manufacture of a reagent for screening for a subject to whom a MELK inhibitor has a high therapeutic effect.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

FIGS. 2A and 2B are pictures showing the result of western blotting using OTSMAb01, which shows MELK expression in various types of cell lines with different MELK expression levels. PK-45P, BT-549, MDA-MB-231, and A549 are MELK high-expressing cell lines and MCF-7, Hep G2, and HT-29 are MELK low-expressing cell lines.

FIG. 2B is a continuation of FIG. 2A.

FIGS. 3A and 3B are photomicrographs showing the specificity of an anti-MELK antibody (OTSMAb01) in immunohistochemical staining using MELK-expressing cell lines. The upper panel shows results of immunohistochemical staining by the anti-MELK antibody of the present invention (OTSMAb01) where staining was detected in paraffin sections prepared from MELK high-expressing cell lines such as PK-45P, BT-549, MDA-MB-231, and A549, whereas hardly any staining was found in MELK low-expressing cell lines such as MCF-7, Hep G2, and HT-29. On the other hand, in the middle panel and bottom panel that shows the results for staining by commercially-available antibodies (MELK(N449)pAb and MELK(HPA017214) pAb), staining was seen in both MELK high-expressing cell lines and low-expressing cell lines. Analysis using cell lines clarified that compared to commercially-available antibodies, the anti-MELK antibody of the present invention (OTSMAb01) had a high specificity in immunohistochemical staining. Furthermore, the graphs below the pictures are graphs plotting calculations of the rate (%) of MELK-positive cells within each of the cell lines as seen with the results of immunohistochemical staining.

FIG. 3B is a continuation of FIG. 3A.

MODE FOR CARRYING OUT THE INVENTION

Detailed Description

Figure 1:
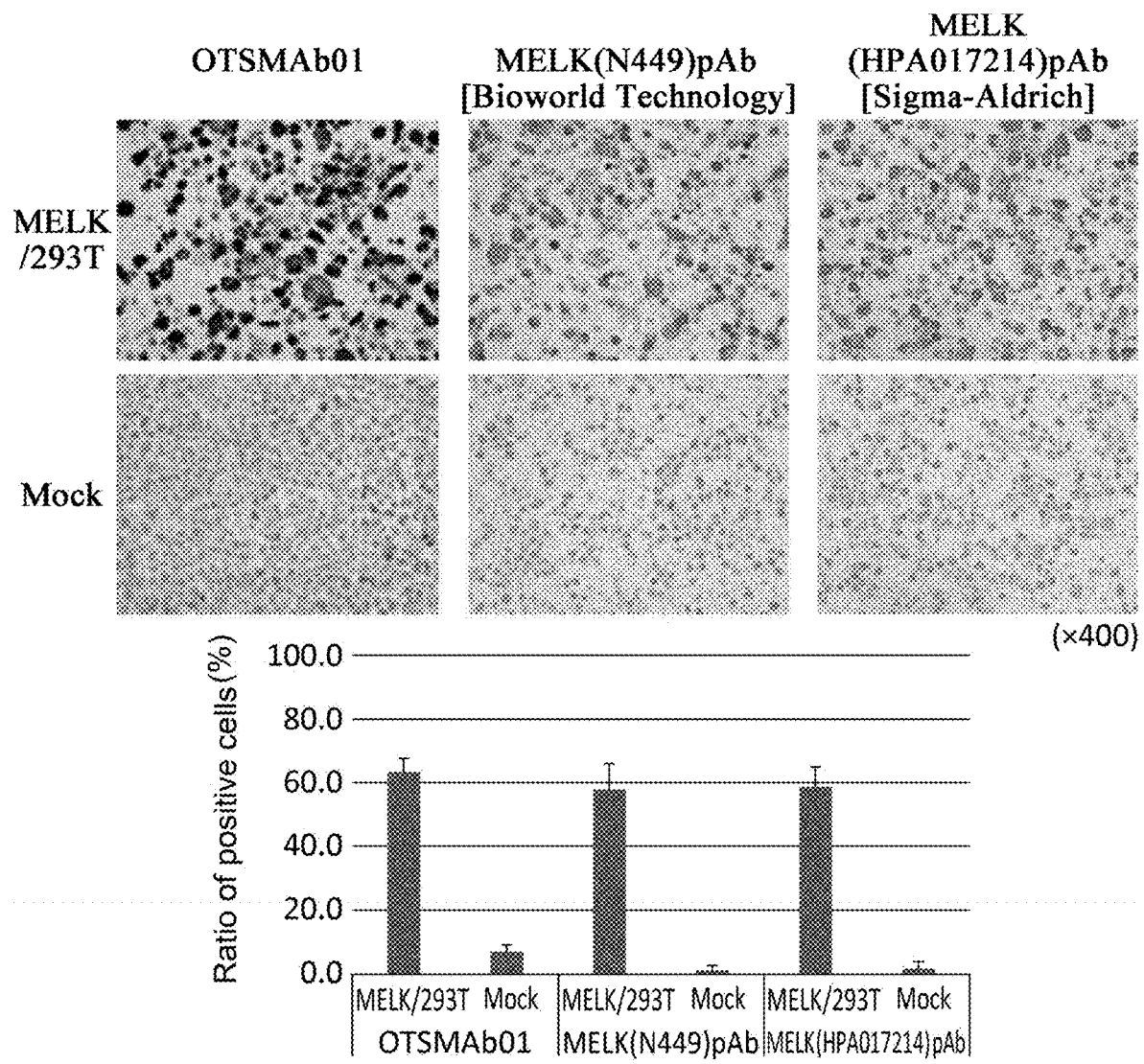
FIG. 1 is a photomicrograph showing the specificity of anti-MELK antibody (OTSMAb01) in immunohistochemical staining using a cell line for a forced-expression system. As a result of immunohistochemical staining using an anti-MELK antibody (OTSMAb01), specific staining was observed in a paraffin section prepared from a MELK forced-expressing cell line (MELK/293T), but no staining was seen in the cell line introduced with an empty vector (Mock/293T) which was used as the negative control. On the other hand, even with the commercially-available antibodies (MELK(N449)pAb (Bioworld Technology) and MELK (HPA017214)pAb (Sigma-Aldrich)), immunohistochemical staining showed that although specific staining was observed in MELK/293T, there was no staining in the Mock. Furthermore, the graph below the pictures is a graph plotting calculations of the rate (%) of MELK-positive cells within the number of cells with forced expression as seen with the results of immunohistochemical staining.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

The present invention provides anti-MELK monoclonal antibodies that can specifically bind to the MELK protein or partial peptides thereof. The present invention provides proof that the anti-MELK monoclonal antibodies of the present invention have high specificity in the detection of the MELK protein by immunohistochemical staining.

The anti-MELK monoclonal antibody of the present invention (OTSMAb01) at least has the following amino acid sequences in the variable regions: OTSMAb01, amino acid sequence of the heavy chain variable region (excluding the signal sequence):

(SEQ ID NO: 7)
EVQLQQSGAELVRPGALVKLSCKASGFNIKDYYMHWVKQRPEQGLEWIGW

IDPENGNTIYDPKFQGKASVTADTSSNTAYLQLSSLTSEDTAVYYCTSHH

YSAMDYWGQGTSVTVSS

OTSMAb01, amino acid sequence of the light chain variable region (excluding the signal sequence):

(SEQ ID NO: 8)
DVVMTQTPLSLPVSLRDQASISCRSSQSLVHSNGNTYLHWYLQKPGQSPK

LLIYKVSNRFSGVPDRFSGSGSGTDFTLIISRVEAEDLGVYFCSQSTYVP

LTFGAGTKLELKRAD

The antibodies of the present invention can also be produced by recombinant techniques using DNAs encoding the above amino acid sequences.

The antibodies of the present invention were obtained from multiple antibody-producing hybridomas obtained by immunizing mice, and conducting a screening and selection of antibodies that have binding ability to MELK, and which show as positive in forced expression cells (positive control cells) and as negative in negative control cells by the immunostaining method. From among the selected antibodies, an antibody that shows as positive in endogenous MELK-expressing cells (positive control cells), and as negative in negative control cells was further selected. When the interaction with MELK is not so strong, antibodies with a weak binding ability would linger around as background. Therefore, by conducting immunostaining using cell lines whose endogenous MELK expression amount were quantified beforehand, and then conducting screening, it was possible to select an antibody that has a strong binding ability with the target MELK.

The antibodies of the present invention bind specifically to MELK. Therefore, the antibodies of the present invention are useful as a tool for detecting MELK or cells or tissues in which MELK is expressed. Furthermore, the antibodies of the present invention can be utilized as a labelled body conjugated to a label that is capable of detecting the antibody, and said labelled body is more preferable, for example, in detecting cancer cells and cancer tissues that express MELK, such as colon cancer. As labels that are conjugated to the antibody of the present invention, it is sufficient as long as the label can detect an antibody bound to MELK, and the labels include affinity labels (for example, biotin, avidin, and such), enzyme labels (for example, horseradish peroxidase, alkaline phosphatase, and such), fluorescent labels (for example, FITC, rhodamine, and such), etc.

When using the antibody of the present invention as a diagnostic agent for selecting patients for cancer treatment, the antibody of the present invention can be used as it is, or can be made into a composition suitable for various types of usage.

I. Definitions

The words "a", "an", and "the" as used herein mean "at least one" unless otherwise specifically indicated.

The terms "isolated" and "purified" used in relation with a substance (for example, peptide, antibody, polynucleotide or such) indicate that the substance does not substantially contain at least one substance that may else be included in a natural source. Thus, an isolated or purified antibody refers to an antibody that does not substantially contain another cellular material, for example, carbohydrate, lipid and other contaminating proteins from the cell or tissue source from which the antibody is derived. In a preferred embodiment, the antibodies of the present invention are isolated or purified.

The terms "polypeptide" and "protein" are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The terms "polynucleotide", "oligonucleotide" and "nucleic acid" are used interchangeably herein, and refer to a polymer of nucleotides.

Unless otherwise specified, the term "MELK-associated disease" refers to a cancer expressing MELK or endometriosis.

Unless otherwise specified, the term "cancer" refers to cancer that overexpresses the MELK gene, and examples include breast cancer, bladder cancer, cervical cancer, cholangiocellular cancer, chronic myelocytic leukemia (CML), colorectal cancer, esophageal cancer, stomach cancer, liver cancer, non-small cell lung cancer (NSCLC), lymphoma, osteosarcoma, ovarian cancer, pancreatic cancer, prostate cancer, kidney cancer, small cell lung cancer (SCLC), and such, but are not limited thereto.

The term "antibody" as used herein is intended to include immunoglobulins and fragments thereof having specific reactivity towards a designated protein or peptides thereof. Antibodies can include those fused with other proteins or labels, and antibody fragments. Furthermore, herein, "antibody" is used in its broadest sense, and specifically, as long as it has the desired biological activity, it includes intact monoclonal antibodies, polyclonal antibodies, multi-specific antibodies made up of at least two intact antibodies (for example, bispecific antibodies), and antibody fragments. "Antibody" refers to all classes (for example, IgA, IgD, IgE, IgQ and IgM).

"Antibody fragment" is a part of an intact antibody and generally comprises one or more antigen-binding regions or variable regions of an intact antibody. Therefore, in the present invention, an antibody fragment can include one or more antigen-binding portions of an intact antibody. The terms "antigen-binding portion" or "antigen-binding fragment" of an antibody as used herein refer to one or more immunologically-active fragments of an antibody that maintain the ability to specifically bind to an antigen (for example, MELK). It has been shown that the antigen-binding function of an antibody may be implemented by fragments of a full-length antibody. Examples of antibody fragments include, Fab, Fab', F(ab')$_2$, and Fv fragments, linear antibodies, and also single-chain antibody molecules. Regardless of the structure, antibody fragments bind to the same antigen as the antigen recognised by an intact antibody. The term "antibody fragment" also includes synthetic polypeptides that bind to specific antigen or genetically-engineered polypeptides, for example, polypeptides consisting of a light chain variable region, "Fv" fragments consisting of a heavy chain and light chain variable regions, recombinant single chain polypeptide molecules where the variable regions of a light chain and heavy chain are linked by a peptide linker ("scFv proteins"), as well as minimal recognising units consisting of amino acid residues imitating hypervariable regions.

Unless otherwise specified, the technical terms and scientific terms used herein all have the same meanings as terms commonly understood by one of ordinary skilled in the art to which the present invention belongs.

In the present invention, the specific binding between the MELK protein and an antibody can be evaluated, for example, by competition between antibodies. Specifically, by using an antibody of the present invention as a reference antibody, for example, an antibody comprising the heavy chain variable region consisting of the amino acid sequence of SEQ ID NO: 7 and the light chain variable region consisting of the amino acid sequence of SEQ ID NO: 8, the specificity of a candidate antibody can be evaluated. A representative reference antibody is OTSMAb01. When a candidate antibody competes with the antigen-antibody reaction between the reference antibody and the human MELK protein, it can be verified that the candidate antibody has a specificity equivalent to the reference antibody. For example, when a reference antibody and the MELK protein is reacted in the presence of a candidate antibody and when the binding of the reference antibody with respect to the amount of the reference antibody that binds to the MELK protein in the absence of the candidate antibody is inhibited by 10%, 20%, 30%, or 40%, more preferably 50%, or more, it can be judged that there is competition between the antibodies. To evaluate the competition between antibodies, not only the MELK protein, but also partial peptides thereof can be used as long as the reference antibody binds to the peptide. Preferable partial peptides are, for example, the partial peptide consisting of the amino acid sequence of SEQ ID NO: 9.

II. Antibody Production

The present invention uses anti-MELK monoclonal antibodies. The antibodies are provided by methods well known in the art.

Exemplary antibody-producing techniques used by the present invention are described below.

(i) Monoclonal antibodies

Monoclonal antibodies are obtained from a substantially homogeneous antibody population. Namely, the individual antibodies making up the population are the same, except for natural mutations that can exist in minute amounts. Thus, the modifier "monoclonal" indicates the antibody characteristic of not being a mixture with other antibodies.

For example, monoclonal antibodies can be produced using the hybridoma method that was first described by Kohler et al., Nature, 256: 495 (1975), or by the recombinant DNA method (U.S. Pat. No. 4,816,567).

In the hybridoma method, mice or other suitable host animals, for example, hamsters and such, are immunized with the MELK polypeptide (MELK protein or a partial polypeptide thereof), and lymphocytes that produce, or that can produce, antibodies that specifically bind to the MELK polypeptide are induced. Alternatively, lymphocytes can be immunised in vitro with the MELK polypeptide. Thereafter, the lymphocytes are fused with myeloma cells using suitable fusing agents such as polyethylene glycol to produce hybridomas (Goding, Monoclonal Antibodies: Principles and Practice, pp. 59-103 (Academic Press, 1986)).

The prepared hybridomas are seeded into a suitable culture medium which preferably contains one or more substances that inhibit the proliferation or survival of parent myeloma cells that have not fused, and grown in that medium. For example, when the parent myeloma cells lack the enzyme hypoxanthine-guanine phosphoribosyltransferase (HGPRT or HPRT), the culture medium for hybridomas can typically include hypoxanthine, aminopterin, and thymidine (HAT medium), which substances inhibit the proliferation of HGPRT-deficient cells.

Preferable myeloma cells are those that efficiently fuse, assist a stable and high-level antibody production by selected antibody-producing cells, and are also sensitive to media such as the HAT medium. Preferable myeloma cell lines include mouse myeloma cell lines, for example, those derived from mouse tumors MOPC-21 and MPC-11, which are available from the Salk Institute Cell Distribution Center, San Diego, Calif. USA, as well as SP-2 cells and X63-Ag8-653 cells that are available from the American Type Culture Collection, Manassas, Va., USA. As to the production of human monoclonal antibodies, human myeloma cell lines and mouse-human hetero myeloma cell lines have been described (Kozbor, J. Immunol., 133: 300 1 (1984); Brodeur et al., Monoclonal Antibody Production Techniques and Applications, pp. 51-63 (Marcel Dekker, Inc., New York, 1987)).

The culture medium in which the hybridomas are proliferating is analysed for production of monoclonal antibodies against the antigen. Preferably, the binding specificity of the monoclonal antibody produced by the hybridomas is determined by immunoprecipitation methods or in vitro binding assays such as radioimmunoassay (RIA) or enzyme linked immunosorbent assay (ELISA).

The binding affinity of the monoclonal antibody can be determined by, for example, 3D Scatchard analysis by Munson et al., Anal Biochem. 107: 220-39 (1980).

After identifying hybridomas that produce an antibody with the desired specificity, affinity, and/or activity, this clone can be sub-cloned using limiting dilution and expanded by standard methods (Goding, Monoclonal Antibodies: Principles and Practice, pp. 59-103 (Academic Press, 1986)). Examples of culture media suitable for this purpose include the D-MEM medium and RPMI1640 medium. Furthermore, hybridomas can be grown in vivo as well, such as ascites neoplasms within animals.

Monoclonal antibodies secreted by subclones may be purified to homogeneity. For example, antibody separation and purification can be performed according to separation methods and purification methods used for general proteins. For example, an antibody can be separated and isolated appropriately from medium, ascites, or serum by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D, POROS and Sepharose F. F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel. Marshak et al., Cold Spring Harbor Laboratory Press (1996)). The chromatography procedures can be carried out by liquid-phase chromatography such as HPLC and FPLC.

DNAs encoding monoclonal antibodies can be easily isolated using conventional procedures (for example, using an oligonucleotide probe that can specifically bind to genes encoding heavy and light chains of a mouse antibody), and sequenced. Hybridomas are useful as a preferable source of supply for such DNAs. After the DNAs are isolated, monoclonal antibody synthesis within recombinant host cells can be achieved by placing the DNAs within an expression vector(s) and transfecting it into host cells such as E. coli cells, simian COS cells, Chinese hamster ovary (CHO) cells, myeloma cells and such that do not produce immunoglobulin proteins by other methods. A review regarding recombinant expression of DNAs encoding antibodies within bacterial cells includes Skerra et al., Curr. Opinion in Immunol., 5: 256-262 (1993) and Pluckthun, Immunol. Revs., 130: 151-188 (1992).

Another method for producing a specific antibody or an antibody fragment that shows reactivity towards MELK is screening an expression library encoding immunoglobulin genes or portions thereof expressed within bacteria, using a MELK protein or a partial peptide thereof. For example, it is possible to express within bacteria a complete Fab fragment, VH region, and Fv region using a phage expression library. See, for example, Ward et al., Nature 341: 544-546 (1989); Huse et al., Science 246: 1275-1281 (1989); and McCafferty et al., Nature 348: 552-554 (1990). For example, by screening such a library using a MELK peptide, it is possible to identify immunoglobulin fragments having reactivity towards MELK. Alternatively, SCID-hu mice (available from GenPharm) may also be used to produce antibodies or fragments thereof.

In further embodiment, an antibody or a fragment thereof can also be isolated from antibody phage library prepared using techniques described in McCafferty et al., Nature, 348: 552-554(1990). Clackson et al., Nature, 352: 624-628 (1991) and Marks et al., J. Mol Biol, 222: 581-597 (1991) respectively describe isolation of mouse antibodies and human antibodies using phage libraries. Subsequent publications describe production of high affinity (nM range) human antibodies by chain shuffling (Marks et al., Biotechnology, 10: 779-783 (1992)), as well as Combinatorial infection and in vivo recombination as a strategy to construct extremely large phage libraries (Waterhouse et al., Nuc. Acids. Res., 21: 2265-2266 (1993)). Therefore, these techniques are means that can be carried out as alternatives to conventional monoclonal antibody hybridoma techniques for isolating monoclonal antibodies.

The present invention provides antibodies suitable for diagnosing MELK-associated diseases, for determining the drug efficacy following treatment with a MELK inhibitor, and for screening for subjects to whom a MELK inhibitor has a high therapeutic effect. The present invention succeeded in establishing a mouse monoclonal antibody clone (OTSMAb01) that can detect the MELK protein with a high specificity in immunohistochemical staining. When this antibody clone was used in immunohistochemical staining of breast cancer clinical specimens, it was proved that there was a positive finding in breast cancer specimens, but almost no staining in normal breast specimens. Furthermore, when commercially-available anti-MELK antibodies were used, staining was seen in samples prepared from among MELK high-expressing cell lines and low-expressing cell lines, whereas when using the anti-MELK antibody of the present invention, it was found that specific staining was seen in samples prepared from MELK high-expressing cell lines. Therefore, the antibody of the present invention with such high antigen specificity is useful in selecting patients with a high MELK expression level, and also in selecting patients in whom treatment using MELK inhibitors is likely to be effective.

The amino acid sequences of the heavy chain variable region (H chain V region) and the light chain variable region (L chain V region) of the anti-MELK mouse monoclonal antibody clone of the present invention (OTSMAb01) are shown in SEQ ID NOs: 7 and 8, respectively.

CDRs (complementarity determining regions) comprised in a heavy chain variable region and light chain variable region can be determined according to methods well known in the art. For example, generally used for determining CDRs is the method described in Kabat et al. (Kabat E. A. et al., (1991) Sequence of Proteins of Immunological Interest. 5th Edition) or Chothia et al. (Chothia et al., J. Mol. Biol. (1987) 196; 901-917). CDR 1, 2 and 3 of the heavy chain variable region of the anti-MELK mouse monoclonal antibody clone (OTSMAb01) of the present invention as determined according to the definition of Kabat are shown in SEQ ID NOs: 1, 2 and 3, respectively, and CDR 1, 2 and 3 of the light chain variable region of the clone are shown in SEQ ID NOs: 4, 5 and 6, respectively.

Therefore, the present invention provides:
an antibody or antigen-binding fragment thereof, comprising either one or both of a heavy chain variable region and a light chain variable region and which can bind to a MELK protein or a partial peptide thereof, wherein the heavy chain variable region comprises:
  a CDR1 comprising the amino acid sequence of SEQ ID NO: 1;
  a CDR2 comprising the amino acid sequence of SEQ ID NO: 2; and
  a CDR3 comprising the amino acid sequence of SEQ ID NO: 3;
and wherein the light chain variable region comprises:
  a CDR1 comprising the amino acid sequence of SEQ ID NO: 4;
  a CDR2 comprising the amino acid sequence of SEQ ID NO: 5; and
  a CDR3 comprising the amino acid sequence of SEQ ID NO: 6.

In the present invention, a partial peptide of MELK protein to which an antibody of the present invention binds preferably comprises the amino acid sequence corresponding to positions 264-601 (SEQ ID NO: 9) of the MELK protein (SEQ ID NO: 22), and consists of an amino acid sequence selected from the amino acid sequence of SEQ ID NO: 22. More preferably, the partial peptide of MELK protein in the present invention can consist of the amino acid sequence of SEQ ID NO: 9.

An example of the heavy chain variable region comprising the above-described "CDR1 comprising the amino acid sequence of SEQ ID NO: 1; CDR2 comprising the amino acid sequence of SEQ ID NO: 2; and CDR3 comprising the amino acid sequence of SEQ ID NO: 3" is a heavy chain variable region comprising the amino acid sequence of SEQ ID NO: 7. An example of the light chain variable region comprising the above-described "CDR1 comprising the amino acid sequence of SEQ ID NO: 4; CDR2 comprising the amino acid sequence of SEQ ID NO: 5; and CDR3 comprising the amino acid sequence of SEQ ID NO: 6" is a light chain variable region comprising the amino acid sequence of SEQ ID NO: 8.

Therefore, in one embodiment, the present invention provides an antibody or antigen-binding fragment thereof that comprises either one or both of the heavy chain variable region comprising the amino acid sequence of SEQ ID NO: 7 and the light chain variable region comprising the amino acid sequence of SEQ ID NO: 8.

The antibodies of the present invention can be prepared by conventional methods. For example, the antibody can be prepared according to conventional gene recombination techniques by inserting into a suitable vector a polynucleotide encoding an antibody polypeptide, introducing said vector into a host, and making the host produce the antibodies (for example, see Vandamme, A. M. et al., Eur. J. Biochem. (1990) 192, 767-75).

Nucleotide sequence of a polynucleotide encoding a variable region (V region) of the antibody of the present invention can be inferred from the amino acid sequence of a V region of the antibody of the present invention. As nucleotide sequences encoding the heavy chain variable region (VH) and light chain variable region (VL) of the antibody clone of the present invention, for example, the nucleotide sequences of SEQ ID NOs: 10 and 11 can be used, respectively. A polynucleotide encoding a V region of the antibody of the present invention can be synthesized based on sequence information using conventional methods such as solid phase synthesis techniques (Beaucage SL & Iyer RP, Tetrahedron (1992) 48, 2223-311; Matthes et al., EMBO J (1984) 3, 801-5) and oligonucleotide synthesis techniques (Jones et al., Nature (1986) 321, 522-5).

A polynucleotide encoding an antibody V region is inserted into an expression vector comprising a polynucleotide encoding an antibody constant (C) region.

In order to produce the antibody used in the present invention, a polynucleotide encoding said antibody (antibody gene) is inserted into the expression vector so as to express the antibody gene under the regulation of expression regulating factors (for example, enhancers, promoters). Host cells are transformed using said expression vector to express the antibody.

In the expression of the antibody genes, the polynucleotide encoding the antibody H chain and the polynucleotide encoding the L chain may be inserted into different expression vectors, and thereafter, the obtained recombinant expression vectors are co-transfected into a host cell. Alternatively, the polynucleotide encoding the antibody H chain and the polynucleotide encoding the L chain can be inserted into the same expression vector together, and thereafter, the obtained recombinant expression vector is transfected into a host cell (for example, WO 94/11523).

The antibody genes can be expressed by known methods. In the case of expression in mammalian cells, a conventional useful promoter, the antibody gene to be expressed, and a poly (A) signal (located downstream of the 3' end of the antibody gene) can be functionally linked. For example, human cytomegalovirus immediate-early promoter/enhancer system can be used as a useful promoter/enhancer system.

Other promoter/enhancer systems, for example, those deriving from viruses (for example, retroviruses, polyoma viruses, adenoviruses and simian virus 40 (SV40)), as well as those deriving from mammalian cells (for example, human elongation factor la (HEF1α)) can be used to express the antibody in the present invention.

When using the SV40 promoter/enhancer system, gene expression can be easily done using the method of Mulligan et al. (Nature (1979) 277, 108-14). When using the HEF1αpromoter/enhancer system, gene expression can be easily done using the method of Mizushima et al. (Nucleic Acids Res. (1990) 18, 5322).

When expressing in E. coli, a conventional useful promoter, a signal sequence for secreting the antibody of interest, and the antibody gene can be functionally linked. The lacZ promoter or araB promoter can be used as promoters. When using the lacZ promoter, gene expression can be done by the method of Ward et al. (Nature (1989) 341, 544-6; FASBE J. (1992) 6, 2422-7), and when using the araB promoter, gene expression can be done by the method of Better et al. (Science (1988) 240, 1041-3).

Regarding a signal sequence for secreting the antibody, when secretion of the antibody of interest into the periplasmic space of E. coli is intended, pelB signal sequence (Lei, S. P. et al., J. Bacteriol. (1987) 169, 4379-83) can be used. The antibody secreted into the periplasmic space is isolated and then re-folded so that the antibody takes a suitable steric structure.

A replication origin deriving from viruses (for example, SV40, polyoma viruses, adenoviruses, bovine papillomaviruses (BPV)) or such can be used. In order to increase the gene copy number in a host cell system, the expression vector can additionally include selection marker genes such as aminoglycoside phosphotransferase (APH) gene, thymidine kinase (TK) gene, E. coli hypoxanthine-guanine phosphoribosyl transferase (Ecogpt) gene, and dihydrofolate reductase (dhfr) gene. Regarding the production of the antibody used in the present invention, an arbitrary expression system including eukaryotic and prokaryotic cell systems can be used. Eukaryotic cells include established cell lines of animals (for example, mammals, insects, mold and fungi, and yeasts). Prokaryotic cells include bacterial cells such as E. coli cells. It is preferable that the antibody used in the present invention is expressed in mammalian cells such as CHO cells, COS cells, myeloma cells, BHK cells, Vero cells, and HeLa cells.

Next, the transformed host cells are cultured in vitro or in vivo, and the antibody of interest is produced. Host cells can be cultured using any known methods. The culture media that can be used herein may be DMEM, MEM, RPMI1640 or IMDM media. The culture media may contain serum supplements such as Fetal Calf Serum (FCS).

In addition to the above-mentioned host cells, it is possible to use transgenic animals as hosts in the production of recombinant antibodies. For example, the antibody gene is inserted into a designated site in a gene encoding a protein that is naturally produced within the mother's milk of an animal (for example, β-casein); and a fusion gene is produced. A DNA fragment comprising the fusion gene inserted with the antibody gene is injected into an embryo of non-human animal and this embryo is then introduced into a female animal. The female animal having the embryo inside gives birth to a transgenic non-human animal. The antibody of interest is secreted into the mother's milk of said transgenic non-human animal or its offspring. In order to increase the amount of mother's milk containing said antibody, a suitable hormone can be administered to said transgenic animal (Ebert, K. M. et al., Bio/Technology (1994) 12, 699-702).

An antibody expressed and produced as mentioned above can be isolated from cells or from the body of a host animal, and can be purified. The antibody isolation and purification as used in the present invention can be done using affinity columns. Other conventionally-used methods can also be used for the antibody isolation and purification, and therefore, the methods are not particularly limited. For example, various chromatography, filtration, ultrafiltration, salting out, and dialysis can be used alone or in combination to isolate and purify the antibody of interest (Antibodies A Laboratory Manual. Ed. Harlow, David Lane, Cold Spring Harbor Laboratory, 1988).

(ii) Antibody fragments

Various techniques have been developed for producing antibody fragments. Conventionally, these fragments were obtained via proteolytic digestion of intact antibodies (for example, see Morimoto et al., Journal of Biochemical and Biophysical Methods 24: 107-117 (1992) and Brennan et al., Science, 229: 81 (1985)). However, such fragments can now be directly produced using recombinant host cells. For example, antibody fragments can be isolated from antibody phage libraries. Alternatively, an F(ab')$_2$ fragment can be formed by direct recovery of an Fab'-SH fragment from *E. coli*, and chemical coupling (Carter et al., Bio/Technology 10: 163-167 (1992)). Another approach is to directly isolate an F(ab')$_2$ fragment from a recombinant host cell culture. Other techniques for producing an antibody fragment would be apparent to those skilled in the art. In another embodiment, an optimum antibody is a single chain Fv fragment (scFv). See WO 93/16185; U.S. Pat. Nos. 5,571,894; and 5,587,458. For example, an antibody fragment may be a "linear antibody" as described in, for example, U.S. Pat. No. 5,641,870. Such linear antibody fragments may have monospecificity or bispecificity.

(iii) Labelled antibodies

The antibody of the present invention is optionally conjugated to an affinity label, an enzyme label, a radioisotope label, a fluorescent label or a chemiluminescent label. For example, the presence of a label which is present within a cancer that expresses MELK, and which is detectable, enables determination of the presence or absence of a cancer or tumor within the subject to be diagnosed. Additionally, it is possible to determine disease aggravation by localization of the label within the cancer.

Labels suitable for use include, for example, fluorescent labels such as fluorescein and rhodamine; and enzyme labels such as luciferase. The detectable label/label for detection used can be selected based on the imaging manner used. A conjugate between such a label and an antibody can be prepared using protocols and techniques known in the art. In the present invention, the antibody of the invention may be conjugated to a desired label right before use, or may be provided as an antibody conjugated to a label.

A conjugate between an antibody and a label can be prepared using various bifunctional protein coupling agents such as N-Succinimidyl 3-(2-pyridyldithio)propionate (SPDP), Succinimidyl-4-(N-maleimidomethyl)cyclohexane-1-carboxylate, iminothiolane (IT), bifunctional derivatives of imidoester (for example, Adipimidic acid dimethyl HCL), active esters (for example, Disuccinimidyl suberate), aldehydes (for example, glutaraldehyde), bis-azide compounds (for example, bis-(p-azidobenzoyl) hexanediamine), bis-diazonium derivatives (for example, bis-(p-diazonium benzoyl)-ethylenediamine), diisocyanates (for example, toluene-2,6-diisocyanate), and bis-active fluorine compounds (for example, 1,5-difluoro-2,4-dinitrobenzene). Alternatively, a fusion protein comprising the antibody and label can be prepared, for example, by recombinant techniques or peptide synthesis. Suitable examples of such fusion proteins include fusion proteins between labelling proteins such as ECFP, EYFP, or EGFP and an antibody.

III. Diagnosis of MELK-associated diseases, screening for subjects to whom a MELK inhibitor has a high therapeutic effect (pre-treatment diagnosis), or determination of drug efficacy following treatment with a MELK inhibitor (post-treatment diagnosis)

MELK is useful as a diagnostic marker for MELK-associated diseases, and also as a marker for evaluating the responsiveness of the diseases to a MELK inhibitor and the drug efficacy of said MELK inhibitor. Therefore, the antibodies of the present invention can be used as a reagent for detecting a marker for diagnosing MELK-associated diseases such as cancer, for the screening for subjects to whom a MELK inhibitor has a high therapeutic effect, or for determining the drug efficacy following treatment with a MELK inhibitor.

More specifically, MELK protein in a sample isolated from a subject can be detected using the antibody of the present invention to carry out diagnosis of MELK-associated diseases, screening for subjects to whom a MELK inhibitor has a high therapeutic effect, or determination of the drug efficacy following treatment with a MELK inhibitor. Therefore, the present invention provides methods for diagnosing a MELK-associated disease or the predisposition for developing the disease in a subject, methods for screening for a subject to whom a MELK inhibitor has a high therapeutic effect, and methods for determining the drug efficacy following treatment with a MELK inhibitor, by detecting MELK protein in a sample isolated from a subject, using the antibody of the present invention. These methods comprise the following steps of:

(a) contacting a sample isolated from a subject with the antibody or antigen-binding fragment thereof of the present invention;

(b) detecting MELK protein in the sample by detecting the binding of the sample with the antibody or antigen-binding fragment thereof; and (c) comparing the MELK protein level in the sample with a control.

In a typical embodiment, the above-mentioned sample is a cell or tissue isolated from the above-mentioned subject, preferably, a tissue isolated from said subject. Therefore, usually each of the methods of the present invention is conducted in vitro for samples isolated from subjects. Methods for isolating tissues and cells from subjects using techniques such as biopsies and blood collection are known. It is also possible to use biological samples removed from subjects through medical procedures conducted for treatment (surgeries and such). Cells and tissues isolated from a subject can be suitably treated prior to contact with the antibody. For example, tissue samples obtained from a subject can generally be made into sections after freezing, further fixed using alcohol, formalin and such, and used as samples for immunohistological analysis. Alternatively, after fixing tissue samples, cultured cells, and such by formalin and such, it is possible to obtain sections for immunohistological analysis by paraffin embedding.

The binding of the antibody or antigen-binding fragment thereof of the present invention with a sample, namely, the binding with the antigen protein in the sample, can be detected by a method known to those skilled in the art. More specifically, after contacting the antibody of the present invention with said sample, by removing antibodies that were not bound to MELK protein in the sample by washing, and detecting the antibody remaining in the sample, the binding of the antibody of the present invention and the MELK protein in the sample can be detected. At this time, when the antibody is directly labelled, the presence of the antibody of the present invention bound to the MELK protein can be detected by detecting the label. When the label is a detectable label such as enzymes, fluorescent substances, luminescent substances and particles, such labels can be readily detected. In addition to these, when the antibody of the present invention is labelled (affinity labelled) with an affinity substance (binding substance) such as biotin, the presence of the antibody can be captured by using a binding partner such as labelled avidin. Alternatively, when the antibody of the present invention is not directly labelled, the antibody of the present invention can be detected by using a binding reagent against the antibody. For example, protein A or an antibody against the antibody, after labelling, can be used as an antibody-binding reagent to detect the antibody of the present invention.

In the diagnosis of MELK-associated diseases, in the above-mentioned step (c), when the MELK protein level is high compared to a control level (normal control level, preferably expression level of MELK protein in a sample isolated from a healthy subject who does not suffer from a MELK-associated disease), this indicates that the subject suffers from a MELK-associated disease or is at a risk of developing it.

Furthermore, when screening for a subject to whom a MELK inhibitor has a high therapeutic effect, in the above-mentioned step (c), when the MELK protein level is equivalent to or high compared to a control level (preferably, expression level of MELK protein in a tissue of a subject diagnosed to have a MELK-associated disease), this indicates that the therapeutic effect by a MELK inhibitor is high in the subject.

On the other hand, when determining the drug efficacy following treatment with a MELK inhibitor, in the above-mentioned step (c), when the MELK protein level is low compared to a control level (preferably, expression level of MELK protein in a sample isolated from the subject before drug administration), this indicates that there was drug efficacy in the subject.

Patients shown to have a MELK-associated disease by a diagnostic method of the present invention are likely to become subjects of treatment with a MELK inhibitor. Therefore, following the diagnostic method of the present invention, a MELK inhibitor can be administered to patients shown to have a MELK-associated disease. Alternatively, a MELK inhibitor can also be administered to patients shown to have a possibility of receiving a high therapeutic effect by a MELK inhibitor after screening. Furthermore, when it is shown that a MELK inhibitor had a therapeutic effect in patients who have been administered with the MELK inhibitor, the MELK inhibitor can be administered continually to the same patients.

More specifically, the present invention relates to methods of treating MELK-associated diseases, which comprise the step of identifying one of the patients selected from the group below by methods of the present invention and administering the MELK inhibitor to said patient:
   a patient shown to have a MELK-associated disease by diagnostic methods of the present invention;
   a patient shown to have a possibility of receiving a high therapeutic effect by a MELK inhibitor; and
   a patient who has been administered with a MELK inhibitor, and shown to have received a therapeutic effect by the inhibitor.

In the present invention, known compounds can be used as a MELK inhibitor administered to patients. For example, there are various known compounds that inhibit the enzyme action of MELK (WO 2012/016082; WO 2013/109388; Oncotarget. 2012, 3: 1629-1640; Oncotarget. 2016; 7: 17652-17664).

In the context of the present invention, a control level measured using a biological sample known to not suffer from a MELK-associated disease (for example, noncancerous), is called "normal control level". When the MELK protein level in a sample isolated from a subject is high compared to the normal control level, the subject may be diagnosed to have a MELK-associated disease to be treated.

On the other hand, a control level measured from a biological sample known to suffer from a MELK-associated disease (for example, cancerous), is called "disease control level (for example, cancerous control level)". When the MELK protein level in a sample isolated from a subject prior to treatment with a MELK inhibitor is equivalent to or high compared to the disease control level, the subject may be diagnosed to receive a high therapeutic effect by the MELK inhibitor.

Moreover, when the MELK protein level in a sample isolated from a subject following treatment with a MELK inhibitor is lower than the disease control level of the same subject prior to drug administration, it may be diagnosed that there was drug efficacy by the treatment, namely, that the subject has received a high therapeutic effect by the MELK inhibitor.

In a specific embodiment, normal cells (or tissues) obtained from an unaffected region (for example, noncancerous region) of an organ having a MELK-associated disease (for example, cancer) to be treated may be used as the normal control. In another embodiment, the control level may be determined by statistical methods based on results obtained by analyzing MELK protein levels measured beforehand in samples that derive from subjects whose disease state (for example, cancerous or noncancerous) is known. The control level may be further derived from a database of expression patterns derived from samples (cells or tissues) tested before. When the sample to be evaluated is a tissue sample, it is preferable to use as control sample a sample that derives from the same tissue.

Furthermore, according to one aspect of the present invention, the MELK protein level in a biological sample may be compared with several control levels measured from several reference samples. It is preferable to use control levels measured from reference samples that derive from a tissue type that is similar to the tissue type of the biological sample derived from the subject. Moreover, it is preferable to use standard values of MELK protein level in a population whose disease state is known. The standard value may be obtained using any methods known in the art. For example, a range of a mean value of +/−2 S. D. or a mean value of +/−3 S. D. can be used as standard value.

The MELK protein level in a sample is judged to be high when the level is, for example, 10%, 25%, or 50% higher than the control level or is over 1.1 times, over 1.5 times, over 2.0 times, over 5.0 times, over 10.0 times, or more compared to the control level. The MELK protein level in a sample is judged to be low when the level is, for example, 10%, 25%, or 50% lower than the control level or is more than 1.1 times, more than 1.5 times, more than 2.0 times, more than 5.0 times, more than 10.0 times or more lower than the control level.

In a typical embodiment, MELK-associated disease is a cancer that expresses MELK or endometriosis. Cancer that expresses MELK is, for example, breast cancer, bladder cancer, cervical cancer, cholangiocellular cancer, chronic myelocytic leukemia (CML), colorectal cancer, esophageal cancer, stomach cancer, liver cancer, non-small cell lung cancer (NSCLC), lymphoma, osteosarcoma, ovarian cancer, pancreatic cancer, prostate cancer, kidney cancer, and small cell lung cancer (SCLC), but is not limited thereto.

In a further embodiment, the present invention provides methods for detecting a diagnostic marker for a MELK-associated disease or the predisposition for developing said disease, including the step of detecting, as said diagnostic marker, a MELK protein in a sample using the antibody or antigen-binding fragment thereof of the present invention. It has been elucidated that MELK expression is enhanced in certain types of cancer cells compared to normal tissues. Therefore, if it is possible to specifically detect MELK expression level, it is useful as a diagnostic marker for diseases associated with MELK. In the context of the present invention, a diagnostic marker for a MELK-associated disease or the predisposition for developing said disease is a MELK protein in a sample isolated from a subject, which is detected by the binding between the antibody or antigen-binding fragment thereof of the present invention, and is characterized in that it is shown that said subject suffers from said disease, or is at a risk of developing the disease when MELK expression level is high compared to a control level. Here, said control level is the normal control level, preferably the expression level of MELK protein in a sample isolated from a healthy subject who does not suffer from MELK-associated diseases. Generally, it is preferable that the control level be the expression level in the same tissue as the tissue from which the cancer cells that the diagnostic marker is trying to detect derive from. The present invention also provides antibodies or antigen-binding fragments thereof of the present invention for use in diagnosing a MELK-associated disease, or the predisposition for developing said disease. Alternatively, the present invention provides use of the antibodies or antigen-binding fragments thereof of the present invention in the manufacture of a reagent for diagnosing a MELK-associated disease, or the predisposition for developing said disease.

In addition, the present invention provides methods for detecting a MELK inhibitor treatment responsiveness marker, the methods comprising the step of detecting the MELK protein in a sample as said responsiveness marker, using the antibody or antigen-binding fragment thereof of the present invention. It has been elucidated that MELK expression is specifically enhanced in certain types of cancer cells, and that the proliferation of such cancer cells is suppressed by a MELK inhibitor (WO 2004/031413; WO 2006/016525; WO 2007/013665; WO 2008/023841). In other words, it is possible to predict the responsiveness towards a MELK inhibitor by using MELK expression as an index. This is because, if MELK is expressed at a high level, a suppression effect of cell growth by the MELK inhibitor can be anticipated. Therefore, if it is possible to specifically detect MELK expression level, it will be useful as a MELK inhibitor treatment responsiveness marker. In the context of the present invention, a MELK inhibitor treatment responsiveness marker is a MELK protein in a sample isolated from a subject, which is detected by the binding between the antibody or antigen-binding fragment thereof of the present invention, and is characterized in that it is shown that the therapeutic effect by the MELK inhibitor is high in the subject when MELK expression level is equivalent to or high compared to a control level. Here, said control level is preferably a disease control level, in other words, the MELK protein expression level in a sample isolated from an affected part of the subject known to suffer from a MELK-associated disease, particularly preferably the expression level of MELK protein in a sample isolated before treatment from a subject to whom a MELK inhibitor has a high therapeutic effect.

The present invention further provides the antibodies or antigen-binding fragments thereof of the present invention for use in the screening for a subject to whom a MELK inhibitor has a high therapeutic effect. Alternatively, the present invention provides use of the antibody or antigen-binding fragment thereof of the present invention in the manufacture of a reagent for screening for a subject to whom a MELK inhibitor has a high therapeutic effect.

The present invention also provides methods for detecting a drug efficacy marker for a MELK inhibitor, the methods comprising the step of detecting a MELK protein in a sample using an antibody or antigen-binding fragment thereof of the present invention as said drug efficacy marker. It has been elucidated that MELK expression is specifically enhanced in certain types of cancer cells, and that the proliferation of such cancer cells is suppressed by a MELK inhibitor (WO 2004/031413; WO 2006/016525; WO 2007/013665; WO 2008/023841). Therefore, cancer tissues having such cancer cells can be reduced or killed by a MELK inhibitor. In other words, it is possible to evaluate the drug efficacy of a MELK inhibitor in a subject having such cancer cells using MELK expression level as an index. This is because, if the MELK expression level in a sample isolated from a tissue that has MELK-positive cancer cells is reduced compared to that in a sample isolated prior to treatment with the MELK inhibitor, it is possible to determine that MELK-positive cancer cells decreased due to the MELK inhibitor. Therefore, if it is possible to detect MELK expression level specifically, it would be useful as a drug efficacy marker for a MELK inhibitor. In the context of the present invention, a drug efficacy marker for a MELK inhibitor is a MELK protein in a sample isolated from a subject to whom a MELK inhibitor was administered, which is detected by the binding with an antibody or antigen-binding fragment thereof of the present invention, and characterized in that it is shown that there was a drug efficacy by the MELK inhibitor in said subject when MELK expression level is low compared to the control level. Here, said control level is preferably the expression level of MELK protein in the sample isolated from an affected part of said subject prior to drug administration.

The present invention also provides antibodies or antigen-binding fragments thereof of the present invention for use in determining the drug efficacy following treatment with a MELK inhibitor. Alternatively, the present invention provides use of an antibody or antigen-binding fragment thereof of the present invention in the manufacture of a reagent for determining the drug efficacy following treatment with a MELK inhibitor.

IV. Reagents or kits for diagnosing a MELK-associated disease, for screening for subjects to whom a MELK inhibitor has a high therapeutic effect, or for determining the drug efficacy following treatment with a MELK inhibitor.

The present invention provides reagents or kits for diagnosing a MELK-associated disease, for screening for subjects to whom a MELK inhibitor has a high therapeutic effect, or for determining the drug efficacy following treatment with a MELK inhibitor. Specifically, these kits include an antibody or antigen-binding fragment thereof of the present invention as a reagent for detecting the MELK protein. In one embodiment, the antibody for the reagent or kit for diagnosis of the present invention can be labelled with a fluorescent substance, a luminescent substance, or a radioisotope. Methods for labelling an antibody and for detecting a labelled antibody are well known in the art, and it is possible to use any labels and methods for the present invention.

The present kits can include a combination of an antibody or antigen-binding fragment thereof of the present invention with another marker detection reagent. The present kits can further include positive and negative control reagents regarding MELK, and a secondary antibody for detecting the antibody of the present invention. For example, culture sections or tissue samples of cell lines known to highly express MELK would be helpful as useful positive control reagents. Furthermore, for example, tissue samples obtained from healthy subjects or noncancerous tissues would be helpful as useful negative control reagents. Secondary antibodies for detecting an antibody of the present invention are preferably labelled with a fluorescent substance, luminescent substance, a radioisotope, or an enzyme. The kit of the present invention may further include other materials desirable from a commercial standpoint user's perspective including buffers, diluents, filters, needles, syringes, and package inserts with instructions for use (for example, documents, tapes, CD-ROMs, and such). These reagents and such can be retained into a labelled container. Appropriate containers include bottles, vials, and test tubes. The containers can be made from various materials such as glass and plastic.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skilled in the art can use methods and materials similar or equivalent to those described herein in the practice or testing of the present invention.

All prior art documents cited herein are incorporated by reference in the present specification.

EXAMPLES

Hereinbelow, the present invention is described in more detail with reference to the Examples, but it is not to be construed as being limited thereto.

[Materials and Methods]

Cell culture

A cell line with forced expression of MELK (MELK/293T) was prepared by introducing a MELK expression vector into the human embryonic kidney cell line 293T purchased from GenHunter, and a cell line introduced with an empty vector (Mock/293T) was prepared as the negative control. The cells were maintained in DMEM supplemented with 10% fetal bovine serum (FBS) and 1% penicillin/streptomycin at 37° C. under a 5% $CO_2$ humidified atmosphere. The human breast cancer cell line MCF-7 purchased from ATCC was maintained in MEM supplemented with 10% fetal bovine serum (FBS), 1% penicillin/streptomycin, non-essential amino acids, sodium pyruvate, and insulin at 37° C. under a 5% $CO_2$ humidified atmosphere. The human hepatoma cell line Hep G2 purchased from JCRB was maintained in DMEM supplemented with 10% fetal bovine serum (FBS) and 1% penicillin/streptomycin at 37° C. under a 5% $CO_2$ humidified atmosphere. The human pancreatic cancer cell line PK-45P received from the Institute of Development, Ageing, and Cancer of the Tohoku University, and the human lung cancer cell line A549 purchased from Dainippon Pharma Co., Ltd., were maintained in RPMI1640 supplemented with 10% fetal bovine serum (FBS) and 1% penicillin/streptomycin at 37° C. under a 5% $CO_2$ humidified atmosphere. The human breast cancer cell line BT-549 purchased from ATCC was maintained in RPMI1640 supplemented with 10% fetal bovine serum (FBS), 1% penicillin/streptomycin, HEPES, sodium pyruvate and insulin at 37° C. under a 5% $CO_2$ humidified atmosphere. The human colon cancer cell line HT-29 purchased from ATCC was maintained in McCoy's 5A supplemented with 10% fetal bovine serum (FBS) and 1% penicillin/streptomycin at 37° C. under a 5% $CO_2$ humidified atmosphere. The human breast cancer cell line MDA-MB-231 purchased from ATCC was maintained in L-15 supplemented with 10% fetal bovine serum (FBS) and 1% penicillin/streptomycin at 37° C. under a humidified atmosphere without $CO_2$.

Clinical Specimens

Tissue samples surgically removed from breast cancers (formalin-fixed paraffin sections, frozen tissues), as well as clinical information corresponding to them, were obtained from the Kanagawa Cancer Center after obtaining written informed consent.

Immunohistochemical staining (IHC)

Formalin-fixed paraffin sections of MELK/293T, Mock/293T, MCF-7, Hep G2, HT-29, PK-45P, BT-549, MDA-MB-231, A549 and clinical specimens were immersed three times for three minutes in xylene for deparaffinization, and thereafter, rehydrated by immersing them in 100% Ethanol twice for 1 minute, and then for 1 minute each in 90%, 70%, and 50% ethanol. For antigen activation, sections immersed in the antigen-activating solution, pH 9 (Nichirei Biosciences Inc.) were incubated at 125° C. for 30 seconds. After incubation, these were left to stand for 20 minutes at room temperature, and washed for 5 minutes under running water. After immersing them in 3.0% hydrogen peroxide water for 10 minutes to perform blocking of endogenous peroxidase, they were washed with Wash Buffer (TBS-T (Takara Bio)) three times for 5 minutes. Furthermore, with the aim of blocking non-specific reactions, a suitable amount of Protein Block Solution (Dako) was dropped onto the sections and then left to stand for 10 minutes. The primary antibodies (OTSMAb01, MELK(N449)pAb, MELK(HPA017214) pAb) were respectively dropped in suitable amounts within a humid box, left to stand for 60 minutes, and then washed with the Wash Buffer three times for 5 minutes. Histofine Simple Stain MAX PO (Nichirei Biosciences Inc.) was dropped in suitable amounts as the secondary antibody in a humid box, and left to stand for 30 minutes. These were then washed with the Wash Buffer three times for 5 minutes. The chromogenic reaction was done using the DAB substrate solution (Nichirei Biosciences Inc.). The slide sections were immersed for 20 seconds in haematoxylin (Dako), and washed under running water. Dehydration was done by immersing them in 50%, 70%, and 90% ethanol for 1 minute, respectively, and then immersing them twice for 1 minute in 100% ethanol. Finally, the sections were immersed twice for 3 minutes in xylene for penetration and enclosed using Mount-Quick (DAIDO SANGYO).

RT-PCR

Clinical frozen tissues (breast cancer) were disrupted by immersing the frozen tissue sections in TRIzol Reagent (Invitrogen), and extracted with chloroform. Roughly equivalent volume of 70% ethanol was added to the obtained extract and total RNA was extracted by using RNeasy Mini kit (QIAGEN). cDNA was then synthesized from the total RNA by using a reverse transcriptase, the SuperScript II Reverse Transcriptase (Invitrogen). The PCR reaction was then carried out using ExTaq (Takara Bio) and the cDNA as template. MELK was used as the expression analysis target gene, and β-actin as the housekeeping gene. MELK was amplified by using the MELK-1F: 5'-ATGATCACCT-CACGGCTA-3' (SEQ ID NO: 12), MELK-iR: 5'-AGGTGTTCTGCATAAGG-3' (SEQ ID NO: 13) primer set, and β-actin was amplified by using the Beta-actin Fw: 5'-AGGATGCAGAAGGAGATCAC-3' (SEQ ID NO: 14), Beta-actin Re: 5'-AGAAAGGGTGTAACGCAACT-3' (SEQ ID NO: 15) primer set. The PCR amplification product was electrophoresed with an agarose gel, and expression levels of the MELK gene were compared.

Western blotting

Protein was extracted from MCF-7, Hep G2, HT-29, PK-45P, BT-549, MDA-MB-231 and A549 using RIPA Lysis Buffer. The target proteins were separated using SDS polyacrylamide gel electrophoresis (SDS-PAGE). The separated target proteins were transferred onto nitrocellulose (NC). After blocking non-specific binding on the membrane surface using the blocking solution Block-Ace (DS Pharma Biomedical), this was incubated with the test antibodies that can bind to the target proteins. After washing the excess test antibodies on the membrane using the TBST Wash Buffer, this was incubated with the secondary antibody labelled with peroxidase (HRP) that can bind to the test antibodies, and then, excess secondary antibodies on the membrane were washed using the Wash Buffer. Using the ECL Western blotting detection system (GE Healthcare), detectable chemiluminescence was generated and recorded using film.

Example 1

Preparation of Anti-MELK Monoclonal Antibody (1) Obtaining hybridomas producing anti-MELK antibody Analysis of the immunogenic region of human MELK protein (SEQ ID NO: 22) showed that the total antigenic score shifts favorably at the 264-601 amino acid region (SEQ ID NO: 9) that takes a long loop structure, and that sequence specificity is also favorable, predicting that antigenicity was high (Medical & Biological Laboratories Co, Ltd). Therefore, in order to produce a MELK-specific antibody, a recombinant protein of the 264-601 amino acid region (SEQ ID NO: 9) of human MELK protein (SEQ ID NO: 22) encoded by the human MELK gene (SEQ ID NO: 21) was used as immunogen. The initial immunization was conducted by adding 50 sg of the antigen peptide to Freund Adjuvant, emulsifying this and subcutaneously injecting it into a Balb/c mouse (Japan SLC, Inc.). Immunizations from the second time onwards were conducted by subcutaneously injecting preparation corresponding to 25 sg amount of antigen peptide as prepared similarly. Three days after the final immunization, splenocytes were prepared from the mouse under sterile conditions and fused with mouse myeloma cells SP2/0, using the polyethylene glycol method according to conventional methods.

(2) Selection of hybridoma producing anti-MELK antibody

Anti-MELK antibody was selected by immunohistochemical staining using 293T cell line expressing the fill-length MELK protein (SEQ ID NO: 22). Namely, after the 293T cell line forcedly expressing the full-length MELK protein was formalin-fixed and made into paraffin sections, hybridomas showing a strong reaction with the cell line forcedly expressing MELK (MELK/293T) were selected by performing immunostaining.

Results of immunohistochemical staining of the hybridoma clone OTSMAb01 which was confirmed to produce a MELK-specific antibody at a high level, among hybridomas tested, is shown in FIG. 1. As shown in the pictures and graph of FIG. 1, when stained using OTSMAb01, staining was seen in the paraffin section prepared from the cell line forcedly expressing MELK (MELK/293T) similar to when using the commercially-available anti-MELK polyclonal antibodies MELK(N449)pAb and MELK(HPA017214)pAb, which in other words, showed that the ratio of MELK-positive cells was high. On the other hand, staining was hardly seen in paraffin sections prepared from cell lines introduced with the empty vector (Mock/293T) that was used as a negative control, showing that the ratio of MELK-positive cells was low. These results showed that the hybridoma clone OTSMAb01 is useful as a hybridoma that produces an antibody that specifically detects MELK in immunohistochemical staining.

This hybridoma clone OTSMAb01 was selected as a hybridoma for producing antibody for further experiments. The hybridoma clone OTSMAb01 was cultured on a large scale, and the culture solution was collected 2 to 3 weeks later. Antibody was purified from the culture solution using a Protein A column (GE Healthcare, NJ). Herein, the antibody of the present invention is also referred to as clone OTSMAb01.

Example 2

Evaluation of the Specificity of the Anti-MELK Monoclonal Antibody

Next, using various cell lines with different MELK expression levels, the specificity of OTSMAb01 was evaluated. Namely, by comparing the results of immunohistochemical staining and Western Blotting using OTSMAb01, it was evaluated whether a staining corresponding to the expression level of the MELK protein was seen.

Figure 2A:
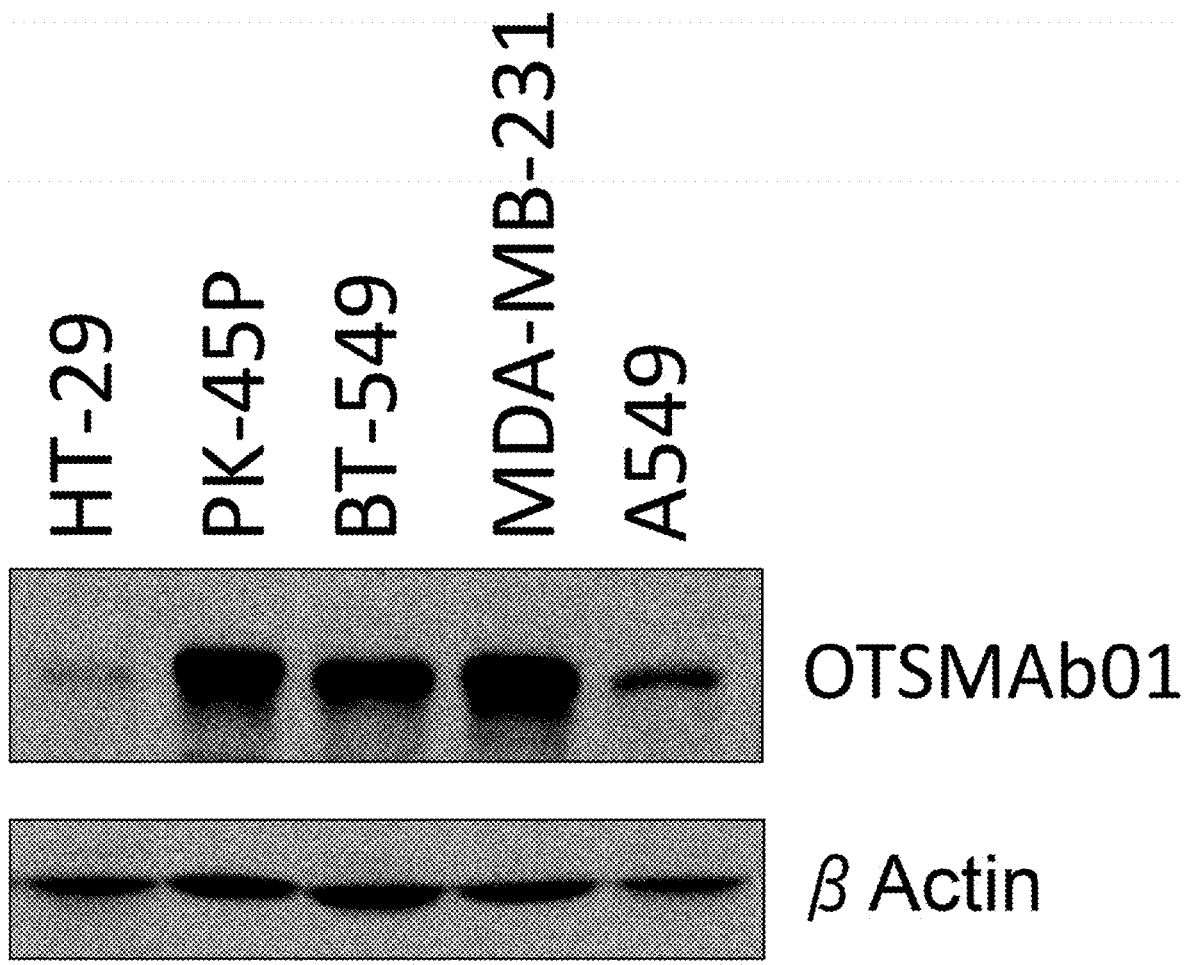
FIG. 2A.
Figure 2B:
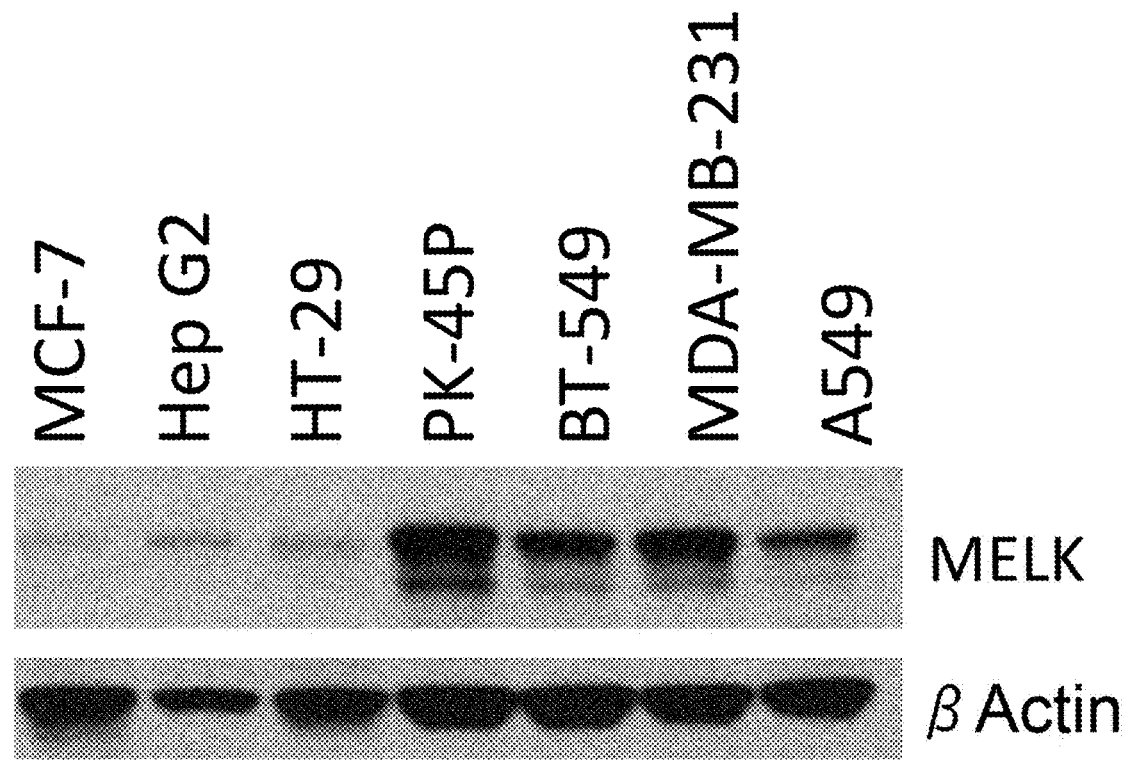

First, endogenous MELK protein expression levels in various human cancer tissue-derived cell lines were verified by Western Blotting using OTSMAb01. As shown in, FIGS. 2A-2B human pancreatic cancer-derived cell line PK-45P, the human breast cancer-derived cell lines BT-549 and MDA-MB-231, and the human lung cancer-derived cell line A549 were MELK high-expressing cell lines, and the human breast cancer-derived cell line MCF-7, the human hepatoma-derived cell line Hep G2, and the human colon cancer-derived cell line HT-29 were MELK low-expressing cell lines.

Figure 3A:
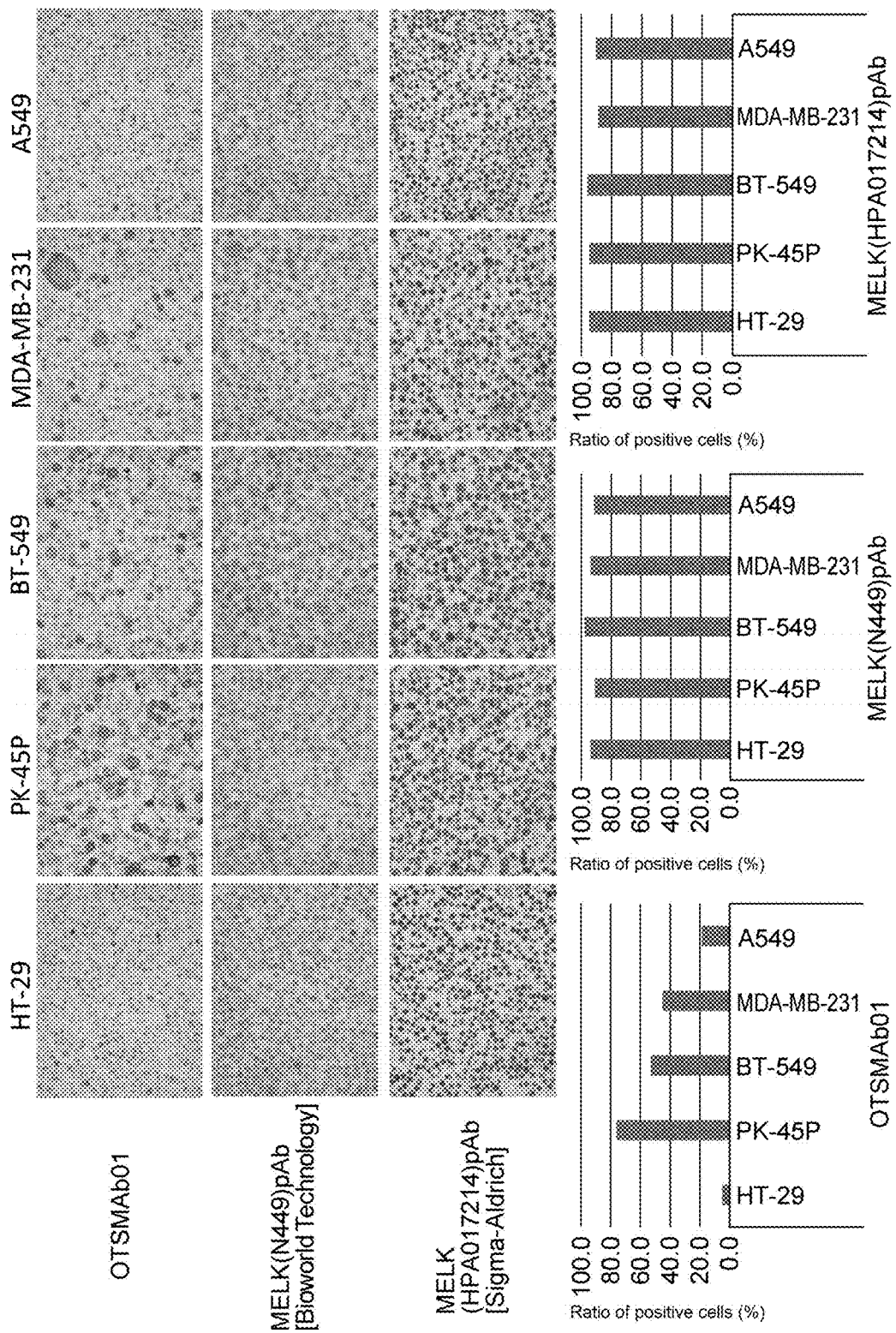
FIG. 3A.
Figure 3B:
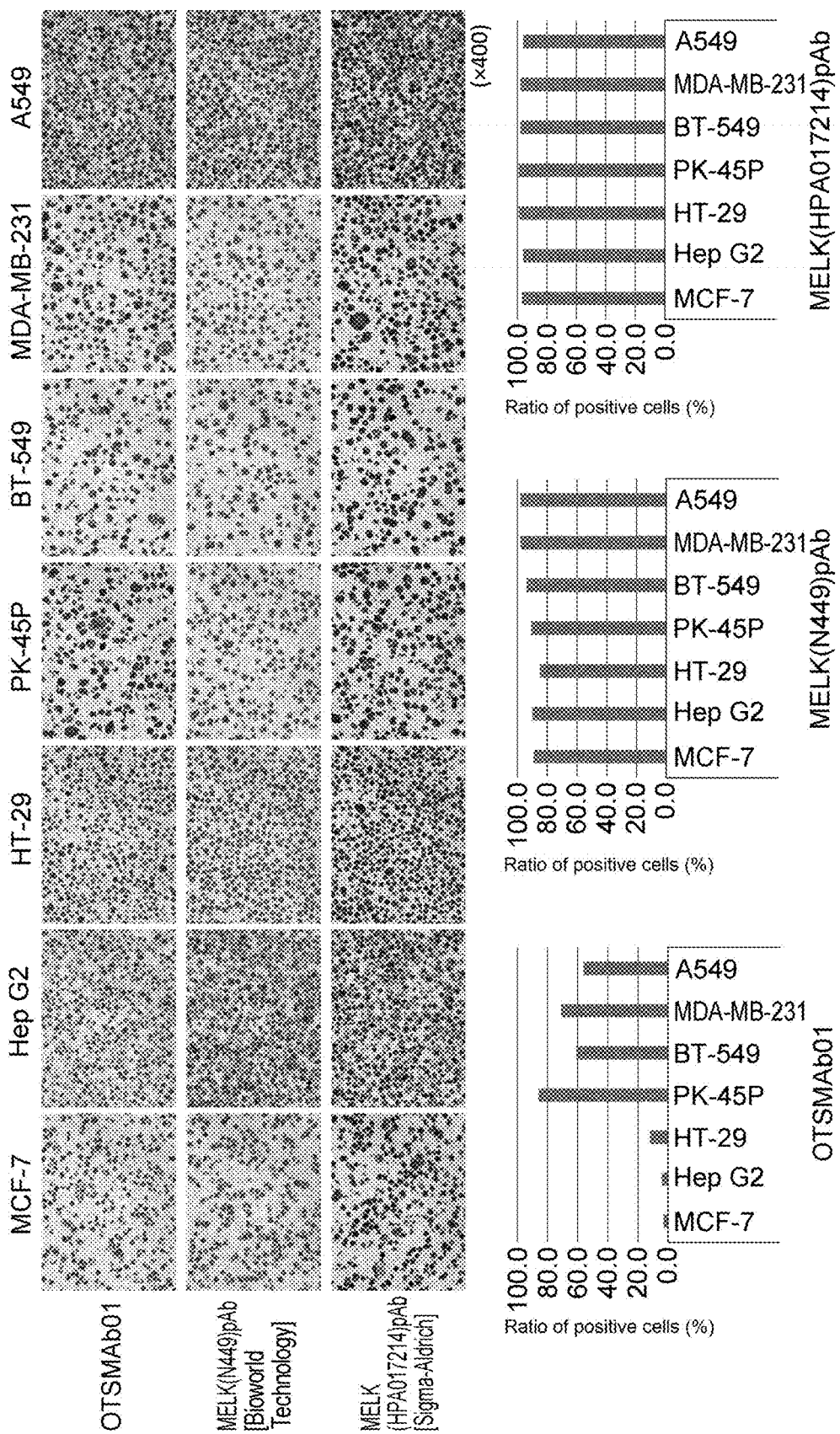

Next, immunohistochemical staining was conducted for paraffin sections prepared from these cell lines by using OTSMAb01 and commercially-available anti-MELK polyclonal antibodies. As shown in FIGS. 3A-3B, when stained using OTSMAb01, staining was seen in paraffin sections prepared from cell lines PK-45P, BT-549, MDA-MB-231 and A549 which were verified to highly express MELK. A positive signal was detected in a high ratio of cells in these paraffin sections. On the other hand, in paraffin sections prepared from MCF-7, Hep G2 and HT-29, which are cell lines having low expression levels of MELK, there was almost no staining, and hardly any positive signal was detected.

On the other hand, when stained using the commercially-available anti-MELK antibodies MELK(N449)pAb (Bioworld Technology) and MELK(HPA017214)pAb (Sigma-Aldrich), a signal was detected in a high ratio of cells in all the cell lines tested, regardless of the expression level of endogenous MELK protein. Therefore, it was suspected that the detection result using these commercially-available antibodies may include false-positive signals.

The above results showed that the anti-MELK antibody of the present invention (OTSMAb01) is a useful tool for obtaining detection results that correlate with the expression level of the MELK protein in a sample by the immunohistochemical staining method, and it was elucidated that it has the advantageous feature of binding to MELK with a high specificity as compared to commercially-available anti-MELK antibodies.

Example 3

Detection of MELK Protein in Clinical Specimens

Figure 4:
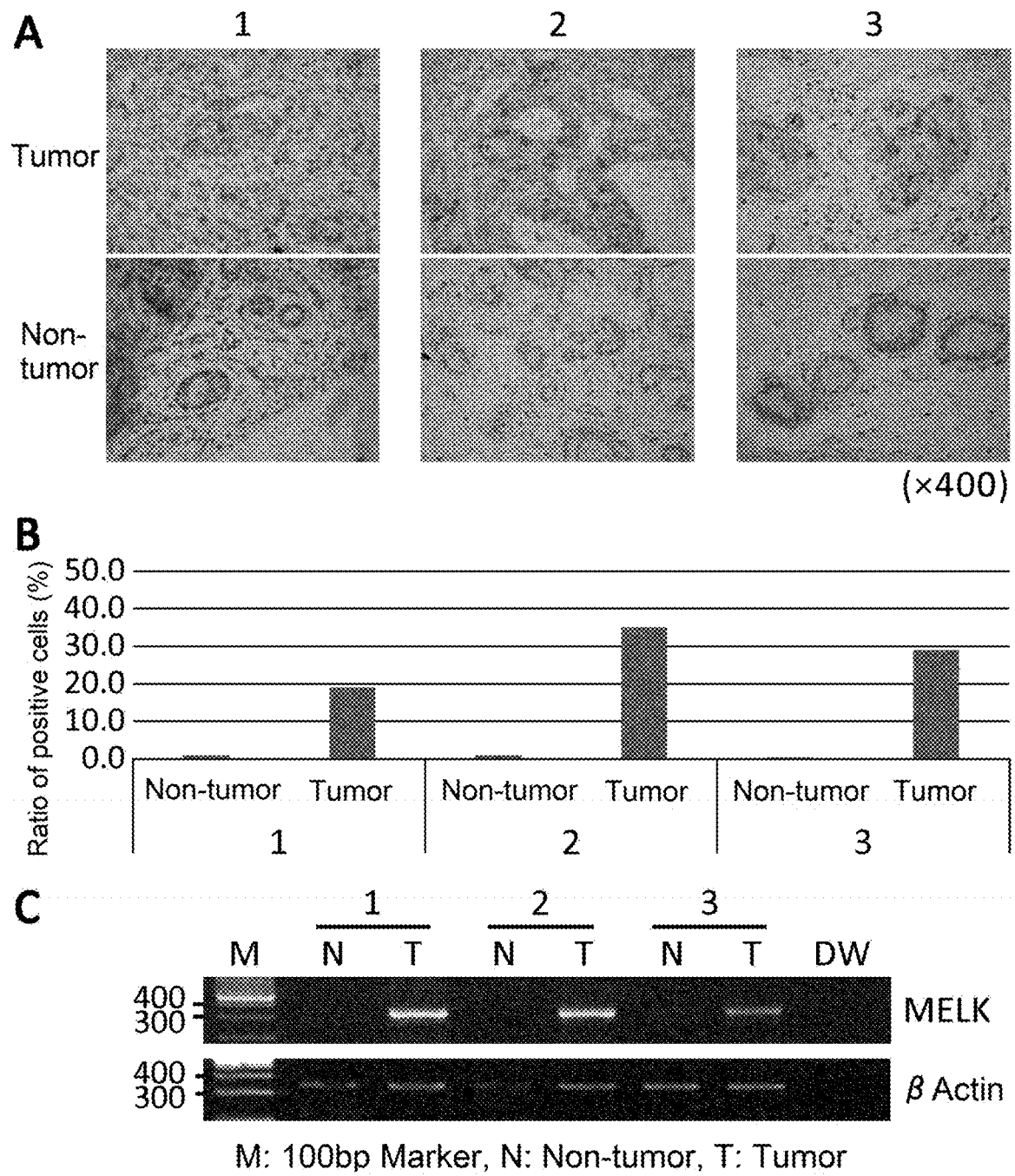
FIG. 4 shows the correlation between expressions in breast cancer clinical specimens 1 to 3 in immunohistochemical staining and semi-quantitative RT-PCR. A: a MELK-positive finding was observed for all the breast cancer specimens by immunohistochemical staining using the anti-MELK antibody of the present invention (OTSMAb01). On the other hand, normal breast specimens were hardly stained. B: From the results of immunohistochemical staining, the rate of MELK-positive cell numbers within the tumor cells was calculated and plotted as a graph. C: Results obtained using expression analysis by RT-PCR of the same clinical cases correlated with immunohistochemical staining. Analysis using clinical specimens elucidated the high specificity of the anti-MELK antibody of the present invention (OTSMAb01) in immunohistochemical staining.

The specificity of the anti-MELK antibody of the present invention (OTSMAb01) in immunohistochemical staining was evaluated using breast cancer clinical specimens. FIG. 4 shows the result of detecting the expression of the MELK protein and RNA in tumor and non-tumor regions in breast cancer clinical specimens 1 to 3, using immunohistochemical staining and semi-quantitative RT-PCR, respectively. As shown in FIG. 4, cells stained with OTSMAb01, namely MELK-positive cells, were detected in tumor regions where MELK RNA expression was verified, but almost no staining was seen in non-tumor regions where MELK RNA expression was not verified, that is, MELK-positive cells were not detected. This result demonstrates that OTSMAb01 can specifically detect the MELK protein even in clinical specimens.

Example 4

The analysis of the amino acid sequences of the variable regions of the anti-MELK monoclonal antibody The amino acid sequences of variable regions of the anti-MELK antibody of the present invention (OTSMAb01) were analysed.

Total RNA was extracted from hybridoma OTSMAb01 using the RNeasy mini kit (QIAGEN). Then cDNA was synthesized from total RNA using Super Script II Reverse Transcriptase (Invitrogen). The primers for cDNA synthesis were as follows:

Heavy chain 3'-primer mIGCUniRv:

```
                                    (SEQ ID NO: 16)
5'-CTGGGAAGGTGTGCACAC-3'
```

Light chain 3'-primer mIGKRv2:

```
                                    (SEQ ID NO: 17)
5'-GTTGTTCAAGAAGCACACGAC-3'
``` dC polymer was added to the cDNA end using 5' RACE System for Rapid Amplification of cDNA Ends (Invitrogen), and polynucleotides encoding the variable regions of the monoclonal antibody were amplified using Platinum Taq DNA Polymerase High Fidelity (Invitrogen). The primers for amplification are as follows. The nucleotide "I" within the primer sequence indicates Inosine.

Heavy chain 5'- and light chain Y-primer 5' RACE Abridged Anchor Primer:

```
                                    (SEQ ID NO: 18)
5'-GGCCACGCGTCGACTAGTACGGGIIGGGIIGGGIIG-3';
```

Heavy chain Y-primer mIGCUniRv2:

```
                                    (SEQ ID NO: 19)
5'-TGGACAGGGATCCAGAGTTCC-3';
``` and

Light chain Y-primer mIGKNesRv2:

```
                                    (SEQ ID NO: 20)
5'-CAGATGTTAACTGCTCACTGGATGG-3'.
```

The PCR products were cloned into pGEM-T Easy Vector (Promega). The insertion fragment regions were sequenced to determine the nucleotide sequences of the variable regions (excluding the signal sequences) of OTSMAb01.

The amino acid sequences and nucleotide sequences of the heavy chain variable region and light chain variable region of the mouse monoclonal antibody were determined as follows:

OTSMAb01, Heavy chain variable region amino acid sequence (excluding the signal sequence): EVQLQQS-GAELVRPGALVKLSCK-ASGFNIKDYYMHWVKQRPEQGLEWIGWIDPENGNT IYDPKFQGKASVTADTSSNTAYLQLSSLTSED-TAVYYCTSHHYSAMDYWGQGTSVTVSS (SEQ ID NO:7) (encoded by the nucleotide sequence of SEQ ID NO: 10)

OTSMAb01, Heavy chain variable region nucleotide sequence:

```
                                    (SEQ ID NO: 10)
5'-GAGGTTCAGCTGCAGCAGTCTGGGGCTGAGCTTGTGAGGCCAGGGGC

CTTAGTCAAGTTGTCCTGCAAAGCTTCTGGCTTCAACATTAAAGACTACT

ATATGCACTGGGTGAAGCAGAGGCCTGAACAGGGCCTGGAGTGGATTGGA
```

```
TGGATTGATCCTGAGAATGGTAATACTATATATGACCCGAAGTTCCAGGG

CAAGGCCAGTGTAACAGCAGACACATCCTCCAACACAGCCTACCTGCAGC

TCAGCAGCCTGACATCTGAGGACACTGCCGTCTATTACTGTACTAGTCAC

CATTACTCTGCTATGGACTACTGGGGTCAAGGAACCTCAGTCACCGTCTC

CTCA-3'
```

OTSMAb01, Light chain variable region amino acid sequence (excluding the signal sequence):
(encoded by the nucleotide sequence of SEQ ID NO: 11)

```
                                            (SEQ ID NO: 8)
DVVMTQTPLSLPVSLRDQASISCRSSQSLVHSNGNTYLHWYLQKPGQSPK

LLIYKVSNRFSGVPDRFSGSGSGTDFTLIISRVEAEDLGVYFCSQSTYVP

LTFGAGTKLELKRAD
```

OTSMAb01, Light chain variable region nucleotide sequence:

```
                                           (SEQ ID NO: 11)
5'-GATGTTGTGATGACCCAAACTCCACTCTCCCTGCCTGTCAGTCTTAG

AGATCAAGCCTCCATCTCTTGCAGATCTAGTCAGAGCCTTGTACACAGTA

ATGGAAACACCTATTTACATTGGTACCTGCAGAAGCCAGGCCAGTCTCCA

AAACTCCTGATCTACAAAGTTTCCAACCGATTTTCTGGGGTCCCAGACAG

GTTCAGTGGCAGTGGATCAGGGACAGATTTCACACTCATAATCAGCAGAG

TGGAGGCTGAGGATCTGGGAGTTTATTTCTGCTCTCAAAGTACATATGTT

CCGCTCACGTTCGGTGCTGGGACCAAGCTGGAGCTGAAACGGGCTGAT-
3'
```

CDR sequences of the antibody of the present invention (OTSMAb01) determined according to the Kabat definition are as follows:
Heavy chain CDR1 (CDR-H1): DYYMH (SEQ ID NO: 1);
Heavy chain CDR2 (CDR-H2): WIDPENGNTIYDPKFQG (SEQ ID NO: 2);
Heavy chain CDR3 (CDR-H3): HHYSAMDY (SEQ ID NO: 3);
Light chain CDR1 (CDR-L1): RSSQSLVHSNGNTYLH (SEQ ID NO: 4);
Light chain CDR2 (CDR-L2): KVSNRFS (SEQ ID NO: 5); and
Light chain CDR3 (CDR-L3): SQSTYVPLT (SEQ ID NO: 6).

INDUSTRIAL APPLICABILITY

The present invention succeeded in producing anti-MELK antibodies capable of detecting the MELK protein in samples isolated from subjects, such as clinical specimens, with a high specificity. By using the anti-MELK antibodies of the present invention, it is possible to detect the MELK protein in a sample with a high sensitivity and low background. Therefore, the antibodies of the present invention are useful in diagnosing MELK-associated diseases such as MELK-expressing cancer. Furthermore, as the antibodies of the present invention can detect MELK according to the expression level of MELK in the samples, it is also useful in the screening for subjects to whom a MELK inhibitor has a high therapeutic effect (pre-treatment diagnosis) and for determining the drug efficacy following treatment with a MELK inhibitor in subjects (post-treatment diagnosis).

The invention claimed is:

1. An antibody or antigen-binding fragment thereof, which can bind MELK protein or a partial peptide thereof, and which comprises both of:
   a heavy chain variable region comprising
   a CDR1 comprising the amino acid sequence of SEQ ID NO: 1,
   a CDR2 comprising the amino acid sequence of SEQ ID NO: 2, and
   a CDR3 comprising the amino acid sequence of SEQ ID NO: 3, and a light chain variable region comprising
   a CDR1 comprising the amino acid sequence of SEQ ID NO: 4,
   a CDR2 comprising the amino acid sequence of SEQ ID NO: 5, and
   a CDR3 comprising the amino acid sequence of SEQ ID NO: 6.

2. The antibody or antigen-binding fragment thereof of claim 1, comprising both of a heavy chain variable region comprising the amino acid sequence of SEQ ID NO: 7 and a light chain variable region comprising the amino acid sequence of SEQ ID NO: 8.

3. The antibody or antigen-binding fragment thereof of claim 1, which specifically recognizes the polypeptide consisting of the amino acid sequence of SEQ ID NO: 9.

4. The antibody or antigen-binding fragment thereof of claim 1, which is conjugated with an affinity label, enzyme label, radioisotope label, or fluorescent label.

5. A polynucleotide encoding the antibody or antigen-binding fragment thereof of claim 1.

6. A reagent comprising the antibody of antigen-binding fragment thereof of claim 1.

7. A method for detecting the expression level of MELK in a subject, comprising the steps of:
 (a) contacting a sample comprising cancer cells or cancer tissues isolated from said subject with the antibody or antigen-binding fragment thereof of claim 1;
 (b) detecting MELK protein in said sample by detecting the binding of said sample with said antibody or antigen-binding fragment thereof; and
 (c) comparing the MELK protein level is said sample with a control, wherein it is indicated that said subject suffers from said cancer expressing MELK, when the MELK protein level is high compared to the control, and wherein the control is the expression level of MELK protein in a sample isolated from a healthy subject who does not have a cancer expressing MELK.

8. The method of claim 7, wherein said cancer is selected from the group consisting of breast cancer, bladder cancer, cervical cancer, cholangiocellular cancer, chronic myclocytic leukemia (CML), colorectal cancer, esophageal cancer, stomach cancer, liver cancer, non-small cell lung cancer (NSCLC), lymphoma, osteosarcoma, ovarian cancer, pancreatic cancer, prostate cancer, kidney cancer, and small cell lung cancer (SCLC).

9. A method for detecting MELK protein in a sample, comprising the steps of:
 (a) contacting a sample isolated from a subject with the antibody or antigen-binding fragment thereof of claim 1; and
 (b) detecting MELK protein in said sample by detecting the binding of said sample with said antibody or antigen-binding fragment thereof.

10. A method for producing an antibody that can bind to MELK protein, or to a partial peptide thereof, comprising the steps of:
 (a) culturing a cell comprising a vector inserted with the polynucleotide of claim 5; and
 (b) recovering said antibody from the cell culture or culture medium.

* * * * *

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: VH CDR1

<400> SEQUENCE: 1

Asp Tyr Tyr Met His
1               5

<210> SEQ ID NO 2
<211> LENGTH: 17
<212> TYPE: PRT
<213> ORGANISM: Artificial Sequence
<220> FEATURE:
<223> OTHER INFORMATION: VH CDR2

<400> SEQUENCE: 2

Trp Ile Asp Pro Glu Asn Gly Asn Thr Ile Tyr Asp Pro Lys Phe Gln
1               5                   10                  15

Gly
```

```
<210> SEQ ID NO 3
<211> LENGTH: 8
<212> TYPE: PRT
<213> ORGANISM: Artificial Sequence
<220> FEATURE:
<223> OTHER INFORMATION: VH CDR3

<400> SEQUENCE: 3

His His Tyr Ser Ala Met Asp Tyr
1               5

<210> SEQ ID NO 4
<211> LENGTH: 16
<212> TYPE: PRT
<213> ORGANISM: Artificial Sequence
<220> FEATURE:
<223> OTHER INFORMATION: VL CDR1

<400> SEQUENCE: 4

Arg Ser Ser Gln Ser Leu Val His Ser Asn Gly Asn Thr Tyr Leu His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: VL CDR2

<400> SEQUENCE: 5

Lys Val Ser Asn Arg Phe Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR

<400> SEQUENCE: 6

Ser Gln Ser Thr Tyr Val Pro Leu Thr
1               5

<210> SEQ ID NO 7
<211> LENGTH: 117
<212> TYPE: PRT
<213> ORGANISM: Artificial Sequence
<220> FEATURE:
<223> OTHER INFORMATION: H-chain variable region

<400> SEQUENCE: 7

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30

Tyr Met His Trp Val Lys Gln Arg Pro Glu Gln Gly Leu Glu Trp Ile
            35                  40                  45

Gly Trp Ile Asp Pro Glu Asn Gly Asn Thr Ile Tyr Asp Pro Lys Phe
        50                  55                  60

Gln Gly Lys Ala Ser Val Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95
```

Thr Ser His His Tyr Ser Ala Met Asp Tyr Trp Gly Gln Gly Thr Ser
              100                 105                 110

Val Thr Val Ser Ser
            115

<210> SEQ ID NO 8
<211> LENGTH: 115
<212> TYPE: PRT
<213> ORGANISM: Artificial Sequence
<220> FEATURE:
<223> OTHER INFORMATION: L-chain variable region

<400> SEQUENCE: 8

Asp Val Val Met Thr Gln Thr Pro Leu Ser Leu Pro Val Ser Leu Arg
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Ile Ile
65                  70                  75                  80

Ser Arg Val Glu Ala Glu Asp Leu Gly Val Tyr Phe Cys Ser Gln Ser
                85                  90                  95

Thr Tyr Val Pro Leu Thr Phe Gly Ala Gly Thr Lys Leu Glu Leu Lys
            100                 105                 110

Arg Ala Asp
        115

<210> SEQ ID NO 9
<211> LENGTH: 338
<212> TYPE: PRT
<213> ORGANISM: Artificial Sequence
<220> FEATURE:
<223> OTHER INFORMATION: MELK fragment for immunogen

<400> SEQUENCE: 9

Met Gln Asp Tyr Asn Tyr Pro Val Glu Trp Gln Ser Lys Asn Pro Phe
1               5                   10                  15

Ile His Leu Asp Asp Cys Val Thr Glu Leu Ser Val His His Arg
            20                  25                  30

Asn Asn Arg Gln Thr Met Glu Asp Leu Ile Ser Leu Trp Gln Tyr Asp
        35                  40                  45

His Leu Thr Ala Thr Tyr Leu Leu Leu Ala Lys Lys Ala Arg Gly
    50                  55                  60

Lys Pro Val Arg Leu Arg Leu Ser Ser Phe Ser Cys Gly Gln Ala Ser
65                  70                  75                  80

Ala Thr Pro Phe Thr Asp Ile Lys Ser Asn Asn Trp Ser Leu Glu Asp
                85                  90                  95

Val Thr Ala Ser Asp Lys Asn Tyr Val Ala Gly Leu Ile Asp Tyr Asp
            100                 105                 110

Trp Cys Glu Asp Asp Leu Ser Thr Gly Ala Ala Thr Pro Arg Thr Ser
            115                 120                 125

Gln Phe Thr Lys Tyr Trp Thr Glu Ser Asn Gly Val Glu Ser Lys Ser
        130                 135                 140

Leu Thr Pro Ala Leu Cys Arg Thr Pro Ala Asn Lys Leu Lys Asn Lys
145                 150                 155                 160

Glu Asn Val Tyr Thr Pro Lys Ser Ala Val Lys Asn Glu Glu Tyr Phe
            165                 170                 175
Met Phe Pro Glu Pro Lys Thr Pro Val Asn Lys Asn Gln His Lys Arg
            180                 185                 190
Glu Ile Leu Thr Thr Pro Asn Arg Tyr Thr Thr Pro Ser Lys Ala Arg
            195                 200                 205
Asn Gln Cys Leu Lys Glu Thr Pro Ile Lys Ile Pro Val Asn Ser Thr
210                 215                 220
Gly Thr Asp Lys Leu Met Thr Gly Val Ile Ser Pro Glu Arg Arg Cys
225                 230                 235                 240
Arg Ser Val Glu Leu Asp Leu Asn Gln Ala His Met Glu Glu Thr Pro
                245                 250                 255
Lys Arg Lys Gly Ala Lys Val Phe Gly Ser Leu Glu Arg Gly Leu Asp
            260                 265                 270
Lys Val Ile Thr Val Leu Thr Arg Ser Lys Arg Lys Gly Ser Ala Arg
            275                 280                 285
Asp Gly Pro Arg Arg Leu Lys Leu His Tyr Asn Val Thr Thr Thr Arg
            290                 295                 300
Leu Val Asn Pro Asp Gln Leu Leu Asn Glu Ile Met Ser Ile Leu Pro
305                 310                 315                 320
Lys Lys His Val Asp Phe Val Gln Lys Gly Tyr Thr Leu Lys Cys Gln
                325                 330                 335

Thr Gln

<210> SEQ ID NO 10
<211> LENGTH: 351
<212> TYPE: DNA
<213> ORGANISM: Artificial Sequence
<220> FEATURE:
<223> OTHER INFORMATION: H-chain variable region nucleic acid sequence

<400> SEQUENCE: 10
gaggttcagc tgcagcagtc tggggctgag cttgtgaggc caggggcctt agtcaagttg     60
tcctgcaaag cttctggctt caacattaaa gactactata tgcactgggt gaagcagagg    120
cctgaacagg gcctggagtg gattggatgg attgatcctg agaatggtaa tactatatat    180
gacccgaagt tccagggcaa ggccagtgta acagcagaca catcctccaa cacagcctac    240
ctgcagctca gcagcctgac atctgaggac actgccgtct attactgtac tagtcaccat    300
tactctgcta tggactactg gggtcaagga acctcagtca ccgtctcctc a             351

<210> SEQ ID NO 11
<211> LENGTH: 345
<212> TYPE: DNA
<213> ORGANISM: Artificial Sequence
<220> FEATURE:
<223> OTHER INFORMATION: L-chain variable region nucleic acid sequence

<400> SEQUENCE: 11
gatgttgtga tgacccaaac tccactctcc ctgcctgtca gtcttagaga tcaagcctcc     60
atctcttgca gatctagtca gagccttgta cacagtaatg aaacaccta tttacattgg     120 tacctgcaga agccaggcca gtctccaaaa ctcctgatct acaaagtttc caaccgattt    180
tctggggtcc cagacaggtt cagtggcagt ggatcaggga cagatttcac actcataatc    240
agcagagtgg aggctgagga tctgggagtt tatttctgct ctcaaagtac atatgttccg    300
ctcacgttcg gtgctgggac caagctggag ctgaaacggg ctgat                    345

<210> SEQ ID NO 12
<211> LENGTH: 18
<212> TYPE: DNA
<213> ORGANISM: Artificial Sequence
<220> FEATURE:
<223> OTHER INFORMATION: An artificially synthesized forward primer
      sequence for MELK

<400> SEQUENCE: 12
atgatcacct cacggcta                                                18

<210> SEQ ID NO 13
<211> LENGTH: 17
<212> TYPE: DNA
<213> ORGANISM: Artificial Sequence
<220> FEATURE:
<223> OTHER INFORMATION: An artificially synthesized reverse primer
      sequence for MELK

<400> SEQUENCE: 13
aggtgttctg cataagg                                                 17

<210> SEQ ID NO 14
<211> LENGTH: 20
<212> TYPE: DNA
<213> ORGANISM: Artificial Sequence
<220> FEATURE:
<223> OTHER INFORMATION: An artificially synthesized forward primer
      sequence for beta-actin

<400> SEQUENCE: 14
aggatgcaga aggagatcac                                              20

<210> SEQ ID NO 15
<211> LENGTH: 20
<212> TYPE: DNA
<213> ORGANISM: Artificial Sequence
<220> FEATURE:
<223> OTHER INFORMATION: An artificially synthesized reverse primer
      sequence for beta-actin

<400> SEQUENCE: 15
agaaagggtg taacgcaact                                              20

<210> SEQ ID NO 16
<211> LENGTH: 18
<212> TYPE: DNA
<213> ORGANISM: Artificial Sequence
<220> FEATURE:
<223> OTHER INFORMATION: An artificially synthesized 3' primer sequence
      for VH

<400> SEQUENCE: 16
ctgggaaggt gtgcacac                                                18

<210> SEQ ID NO 17
<211> LENGTH: 21
<212> TYPE: DNA
<213> ORGANISM: Artificial Sequence
<220> FEATURE:
<223> OTHER INFORMATION: An artificially synthesized 3' primer sequence
      for VL

<400> SEQUENCE: 17
gttgttcaag aagcacacga c                                            21

<210> SEQ ID NO 18
<211> LENGTH: 36
<212> TYPE: DNA
<213> ORGANISM: Artificial Sequence
<220> FEATURE:
<223> OTHER INFORMATION: An artificially synthesized 5' primer sequence
      for VH and VL
<220> FEATURE:
<221> NAME/KEY: misc_feature
<222> LOCATION: (24)..(25)
<223> OTHER INFORMATION: n is inosine
<220> FEATURE:
<221> NAME/KEY: misc_feature
<222> LOCATION: (29)..(30)
<223> OTHER INFORMATION: n is inosine
<220> FEATURE:
<221> NAME/KEY: misc_feature
<222> LOCATION: (34)..(35)
<223> OTHER INFORMATION: n is inosine

<400> SEQUENCE: 18
ggccacgcgt cgactagtac gggnngggnn gggnng                            36

<210> SEQ ID NO 19
<211> LENGTH: 21
<212> TYPE: DNA
<213> ORGANISM: Artificial Sequence
<220> FEATURE:
<223> OTHER INFORMATION: An artificially synthesized 3' primer sequence
      for VH

<400> SEQUENCE: 19
tggacaggga tccagagttc c                                            21

<210> SEQ ID NO 20
<211> LENGTH: 25
<212> TYPE: DNA
<213> ORGANISM: Artificial Sequence
<220> FEATURE:
<223> OTHER INFORMATION: An artificially synthesized 3' primer sequence
      for VL

<400> SEQUENCE: 20
cagatgttaa ctgctcactg gatgg                                        25

<210> SEQ ID NO 21
<211> LENGTH: 2486
<212> TYPE: DNA
<213> ORGANISM: Homo sapiens
<220> FEATURE:
<221> NAME/KEY: CDS
<222> LOCATION: (185)..(2140)
<300> PUBLICATION INFORMATION:
<308> DATABASE ACCESSION NUMBER: Genbank acc no. NM_014791.3
<309> DATABASE ENTRY DATE: 2015-09-25
<313> RELEVANT RESIDUES IN SEQ ID NO: (1)..(2486)

<400> SEQUENCE: 21
gagatttgat tcccttggcg ggcggaagcg gccacaaccc ggcgatcgaa aagattctta    60
ggaacgccgt accagccgcg tctctcagga cagcaggccc ctgtccttct gtcgggcgcc   120
gctcagccgt gccctccgcc cctcaggttc tttttctaat tccaaataaa cttgcaagag   180 gact atg aaa gat tat gat gaa ctt ctc aaa tat tat gaa tta cat gaa   229
     Met Lys Asp Tyr Asp Glu Leu Leu Lys Tyr Tyr Glu Leu His Glu
     1               5                   10                  15 act att ggg aca ggt ggc ttt gca aag gtc aaa ctt gcc tgc cat atc    277
Thr Ile Gly Thr Gly Gly Phe Ala Lys Val Lys Leu Ala Cys His Ile
             20                  25                  30

| | | | | | | | | | | | | | | | | |
|---|---|---|---|---|---|---|---|---|---|---|---|---|---|---|---|---|
| ctt | act | gga | gag | atg | gta | gct | ata | aaa | atc | atg | gat | aaa | aac | aca | cta | 325 |
| Leu | Thr | Gly | Glu | Met | Val | Ala | Ile | Lys | Ile | Met | Asp | Lys | Asn | Thr | Leu | |
| | | | 35 | | | | 40 | | | | | 45 | | | | |
| ggg | agt | gat | ttg | ccc | cgg | atc | aaa | acg | gag | att | gag | gcc | ttg | aag | aac | 373 |
| Gly | Ser | Asp | Leu | Pro | Arg | Ile | Lys | Thr | Glu | Ile | Glu | Ala | Leu | Lys | Asn | |
| | 50 | | | | | 55 | | | | | 60 | | | | | |
| ctg | aga | cat | cag | cat | ata | tgt | caa | ctc | tac | cat | gtg | cta | gag | aca | gcc | 421 |
| Leu | Arg | His | Gln | His | Ile | Cys | Gln | Leu | Tyr | His | Val | Leu | Glu | Thr | Ala | |
| 65 | | | | | 70 | | | | | 75 | | | | | | |
| aac | aaa | ata | ttc | atg | gtt | ctt | gag | tac | tgc | cct | gga | gga | gag | ctg | ttt | 469 |
| Asn | Lys | Ile | Phe | Met | Val | Leu | Glu | Tyr | Cys | Pro | Gly | Gly | Glu | Leu | Phe | |
| 80 | | | | 85 | | | | | 90 | | | | | | 95 | |
| gac | tat | ata | att | tcc | cag | gat | cgc | ctg | tca | gaa | gag | gag | acc | cgg | gtt | 517 |
| Asp | Tyr | Ile | Ile | Ser | Gln | Asp | Arg | Leu | Ser | Glu | Glu | Glu | Thr | Arg | Val | |
| | | | 100 | | | | | 105 | | | | | 110 | | | |
| gtc | ttc | cgt | cag | ata | gta | tct | gct | gtt | gct | tat | gtg | cac | agc | cag | ggc | 565 |
| Val | Phe | Arg | Gln | Ile | Val | Ser | Ala | Val | Ala | Tyr | Val | His | Ser | Gln | Gly | |
| | | | 115 | | | | | 120 | | | | | 125 | | | |
| tat | gct | cac | agg | gac | ctc | aag | cca | gaa | aat | ttg | ctg | ttt | gat | gaa | tat | 613 |
| Tyr | Ala | His | Arg | Asp | Leu | Lys | Pro | Glu | Asn | Leu | Leu | Phe | Asp | Glu | Tyr | |
| | | 130 | | | | | 135 | | | | | 140 | | | | |
| cat | aaa | tta | aag | ctg | att | gac | ttt | ggt | ctc | tgt | gca | aaa | ccc | aag | ggt | 661 |
| His | Lys | Leu | Lys | Leu | Ile | Asp | Phe | Gly | Leu | Cys | Ala | Lys | Pro | Lys | Gly | |
| 145 | | | | | 150 | | | | | 155 | | | | | | |
| aac | aag | gat | tac | cat | cta | cag | aca | tgc | tgt | ggg | agt | ctg | gct | tat | gca | 709 |
| Asn | Lys | Asp | Tyr | His | Leu | Gln | Thr | Cys | Cys | Gly | Ser | Leu | Ala | Tyr | Ala | |
| 160 | | | | 165 | | | | | 170 | | | | | 175 | | |
| gca | cct | gag | tta | ata | caa | ggc | aaa | tca | tat | ctt | gga | tca | gag | gca | gat | 757 |
| Ala | Pro | Glu | Leu | Ile | Gln | Gly | Lys | Ser | Tyr | Leu | Gly | Ser | Glu | Ala | Asp | |
| | | | 180 | | | | | 185 | | | | | 190 | | | |
| gtt | tgg | agc | atg | ggc | ata | ctg | tta | tat | gtt | ctt | atg | tgt | gga | ttt | cta | 805 |
| Val | Trp | Ser | Met | Gly | Ile | Leu | Leu | Tyr | Val | Leu | Met | Cys | Gly | Phe | Leu | |
| | | 195 | | | | | 200 | | | | | 205 | | | | |
| cca | ttt | gat | gat | gat | aat | gta | atg | gct | tta | tac | aag | aag | att | atg | aga | 853 |
| Pro | Phe | Asp | Asp | Asp | Asn | Val | Met | Ala | Leu | Tyr | Lys | Lys | Ile | Met | Arg | |
| | | 210 | | | | | 215 | | | | | 220 | | | | |
| gga | aaa | tat | gat | gtt | ccc | aag | tgg | ctc | tct | ccc | agt | agc | att | ctg | ctt | 901 |
| Gly | Lys | Tyr | Asp | Val | Pro | Lys | Trp | Leu | Ser | Pro | Ser | Ser | Ile | Leu | Leu | |
| | 225 | | | | | 230 | | | | | 235 | | | | | |
| ctt | caa | caa | atg | ctg | cag | gtg | gac | cca | aag | aaa | cgg | att | tct | atg | aaa | 949 |
| Leu | Gln | Gln | Met | Leu | Gln | Val | Asp | Pro | Lys | Lys | Arg | Ile | Ser | Met | Lys | |
| 240 | | | | | 245 | | | | | 250 | | | | | 255 | |
| aat | cta | ttg | aac | cat | ccc | tgg | atc | atg | caa | gat | tac | aac | tat | cct | gtt | 997 |
| Asn | Leu | Leu | Asn | His | Pro | Trp | Ile | Met | Gln | Asp | Tyr | Asn | Tyr | Pro | Val | |
| | | | | 260 | | | | | 265 | | | | | 270 | | |
| gag | tgg | caa | agc | aag | aat | cct | ttt | att | cac | ctc | gat | gat | gat | tgc | gta | 1045 |
| Glu | Trp | Gln | Ser | Lys | Asn | Pro | Phe | Ile | His | Leu | Asp | Asp | Asp | Cys | Val | |
| | | | 275 | | | | | 280 | | | | | 285 | | | |
| aca | gaa | ctt | tct | gta | cat | cac | aga | aac | aac | agg | caa | aca | atg | gag | gat | 1093 |
| Thr | Glu | Leu | Ser | Val | His | His | Arg | Asn | Asn | Arg | Gln | Thr | Met | Glu | Asp | |
| | | 290 | | | | | 295 | | | | | 300 | | | | |
| tta | att | tca | ctg | tgg | cag | tat | gat | cac | ctc | acg | gct | acc | tat | ctt | ctg | 1141 |
| Leu | Ile | Ser | Leu | Trp | Gln | Tyr | Asp | His | Leu | Thr | Ala | Thr | Tyr | Leu | Leu | |
| | 305 | | | | | 310 | | | | | 315 | | | | | |
| ctt | cta | gcc | aag | aag | gct | cgg | gga | aaa | cca | gtt | cgt | tta | agg | ctt | tct | 1189 |
| Leu | Leu | Ala | Lys | Lys | Ala | Arg | Gly | Lys | Pro | Val | Arg | Leu | Arg | Leu | Ser | |
| 320 | | | | 325 | | | | | 330 | | | | | 335 | | |
| tct | ttc | tcc | tgt | gga | caa | gcc | agt | gct | acc | cca | ttc | aca | gac | atc | aag | 1237 |
| Ser | Phe | Ser | Cys | Gly | Gln | Ala | Ser | Ala | Thr | Pro | Phe | Thr | Asp | Ile | Lys | |

-continued

```
                  340                 345                 350
tca aat aat tgg agt ctg gaa gat gtg acc gca agt gat aaa aat tat   1285
Ser Asn Asn Trp Ser Leu Glu Asp Val Thr Ala Ser Asp Lys Asn Tyr
            355                 360                 365 gtg gcg gga tta ata gac tat gat tgg tgt gaa gat gat tta tca aca   1333
Val Ala Gly Leu Ile Asp Tyr Asp Trp Cys Glu Asp Asp Leu Ser Thr
        370                 375                 380 ggt gct gct act ccc cga aca tca cag ttt acc aag tac tgg aca gaa   1381
Gly Ala Ala Thr Pro Arg Thr Ser Gln Phe Thr Lys Tyr Trp Thr Glu
385                 390                 395 tca aat ggg gtg gaa tct aaa tca tta act cca gcc tta tgc aga aca   1429
Ser Asn Gly Val Glu Ser Lys Ser Leu Thr Pro Ala Leu Cys Arg Thr
400                 405                 410                 415 cct gca aat aaa tta aag aac aaa gaa aat gta tat act cct aag tct   1477
Pro Ala Asn Lys Leu Lys Asn Lys Glu Asn Val Tyr Thr Pro Lys Ser
                420                 425                 430 gct gta aag aat gaa gag tac ttt atg ttt cct gag cca aag act cca   1525
Ala Val Lys Asn Glu Glu Tyr Phe Met Phe Pro Glu Pro Lys Thr Pro
            435                 440                 445 gtt aat aag aac cag cat aag aga gaa ata ctc act acg cca aat cgt   1573
Val Asn Lys Asn Gln His Lys Arg Glu Ile Leu Thr Thr Pro Asn Arg
        450                 455                 460 tac act aca ccc tca aaa gct aga aac cag tgc ctg aaa gaa act cca   1621
Tyr Thr Thr Pro Ser Lys Ala Arg Asn Gln Cys Leu Lys Glu Thr Pro
465                 470                 475 att aaa ata cca gta aat tca aca gga aca gac aag tta atg aca ggt   1669
Ile Lys Ile Pro Val Asn Ser Thr Gly Thr Asp Lys Leu Met Thr Gly
480                 485                 490                 495 gtc att agc cct gag agg cgg tgc cgc tca gtg gaa ttg gat ctc aac   1717
Val Ile Ser Pro Glu Arg Arg Cys Arg Ser Val Glu Leu Asp Leu Asn
                500                 505                 510 caa gca cat atg gag gag act cca aaa aga aag gga gcc aaa gtg ttt   1765
Gln Ala His Met Glu Glu Thr Pro Lys Arg Lys Gly Ala Lys Val Phe
            515                 520                 525 ggg agc ctt gaa agg ggg ttg gat aag gtt atc act gtg ctc acc agg   1813
Gly Ser Leu Glu Arg Gly Leu Asp Lys Val Ile Thr Val Leu Thr Arg
        530                 535                 540 agc aaa agg aag ggt tct gcc aga gac ggg ccc aga aga cta aag ctt   1861
Ser Lys Arg Lys Gly Ser Ala Arg Asp Gly Pro Arg Arg Leu Lys Leu
545                 550                 555 cac tat aac gtg act aca act aga tta gtg aat cca gat caa ctg ttg   1909
His Tyr Asn Val Thr Thr Thr Arg Leu Val Asn Pro Asp Gln Leu Leu
560                 565                 570                 575 aat gaa ata atg tct att ctt cca aag aag cat gtt gac ttt gta caa   1957
Asn Glu Ile Met Ser Ile Leu Pro Lys Lys His Val Asp Phe Val Gln
                580                 585                 590 aag ggt tat aca ctg aag tgt caa aca cag tca gat ttt ggg aaa gtg   2005
Lys Gly Tyr Thr Leu Lys Cys Gln Thr Gln Ser Asp Phe Gly Lys Val
            595                 600                 605 aca atg caa ttt gaa tta gaa gtg tgc cag ctt caa aaa ccc gat gtg   2053
Thr Met Gln Phe Glu Leu Glu Val Cys Gln Leu Gln Lys Pro Asp Val
        610                 615                 620 gtg ggt atc agg agg cag cgg ctt aag ggc gat gcc tgg gtt tac aaa   2101
Val Gly Ile Arg Arg Gln Arg Leu Lys Gly Asp Ala Trp Val Tyr Lys
625                 630                 635 aga tta gtg gaa gac atc cta tct agc tgc aag gta taa ttgatggatt    2150
Arg Leu Val Glu Asp Ile Leu Ser Ser Cys Lys Val
640                 645                 650 cttccatcct gccggatgag tgtgggtgtg atacagccta cataaagact gttatgatcg  2210
```

-continued

```
ctttgatttt aaagttcatt ggaactacca acttgtttct aaagagctat cttaagacca    2270
atatctcttt gttttaaac aaaagatatt attttgtgta tgaatctaaa tcaagcccat     2330
ctgtcattat gttactgtct tttttaatca tgtggttttg tatattaata attgttgact   2390
ttcttagatt cacttccata tgtgaatgta agctcttaac tatgtctctt tgtaatgtgt   2450
aatttctttc tgaaataaaa ccatttgtga atatag                             2486
```

<210> SEQ ID NO 22
<211> LENGTH: 651
<212> TYPE: PRT
<213> ORGANISM: Homo sapiens

<400> SEQUENCE: 22

```
Met Lys Asp Tyr Asp Glu Leu Leu Lys Tyr Tyr Glu Leu His Glu Thr
  1               5                  10                  15

Ile Gly Thr Gly Gly Phe Ala Lys Val Lys Leu Ala Cys His Ile Leu
                 20                  25                  30

Thr Gly Glu Met Val Ala Ile Lys Ile Met Asp Lys Asn Thr Leu Gly
             35                  40                  45

Ser Asp Leu Pro Arg Ile Lys Thr Glu Ile Glu Ala Leu Lys Asn Leu
         50                  55                  60

Arg His Gln His Ile Cys Gln Leu Tyr His Val Leu Glu Thr Ala Asn
     65                  70                  75                  80

Lys Ile Phe Met Val Leu Glu Tyr Cys Pro Gly Gly Glu Leu Phe Asp
                 85                  90                  95

Tyr Ile Ile Ser Gln Asp Arg Leu Ser Glu Glu Glu Thr Arg Val Val
                100                 105                 110

Phe Arg Gln Ile Val Ser Ala Val Ala Tyr Val His Ser Gln Gly Tyr
            115                 120                 125

Ala His Arg Asp Leu Lys Pro Glu Asn Leu Leu Phe Asp Glu Tyr His
        130                 135                 140

Lys Leu Lys Leu Ile Asp Phe Gly Leu Cys Ala Lys Pro Lys Gly Asn
145                 150                 155                 160

Lys Asp Tyr His Leu Gln Thr Cys Cys Gly Ser Leu Ala Tyr Ala Ala
                165                 170                 175

Pro Glu Leu Ile Gln Gly Lys Ser Tyr Leu Gly Ser Glu Ala Asp Val
            180                 185                 190

Trp Ser Met Gly Ile Leu Leu Tyr Val Leu Met Cys Gly Phe Leu Pro
        195                 200                 205

Phe Asp Asp Asp Asn Val Met Ala Leu Tyr Lys Lys Ile Met Arg Gly
    210                 215                 220

Lys Tyr Asp Val Pro Lys Trp Leu Ser Pro Ser Ser Ile Leu Leu Leu
225                 230                 235                 240

Gln Gln Met Leu Gln Val Asp Pro Lys Lys Arg Ile Ser Met Lys Asn
                245                 250                 255

Leu Leu Asn His Pro Trp Ile Met Gln Asp Tyr Asn Tyr Pro Val Glu
            260                 265                 270

Trp Gln Ser Lys Asn Pro Phe Ile His Leu Asp Asp Asp Cys Val Thr
        275                 280                 285

Glu Leu Ser Val His His Arg Asn Asn Arg Gln Thr Met Glu Asp Leu
    290                 295                 300

Ile Ser Leu Trp Gln Tyr Asp His Leu Thr Ala Thr Tyr Leu Leu Leu
305                 310                 315                 320
```

```
Leu Ala Lys Lys Ala Arg Gly Lys Pro Val Arg Leu Arg Leu Ser Ser
            325                 330                 335

Phe Ser Cys Gly Gln Ala Ser Ala Thr Pro Phe Thr Asp Ile Lys Ser
            340                 345                 350

Asn Asn Trp Ser Leu Glu Asp Val Thr Ala Ser Asp Lys Asn Tyr Val
            355                 360                 365

Ala Gly Leu Ile Asp Tyr Asp Trp Cys Glu Asp Leu Ser Thr Gly
            370             375             380

Ala Ala Thr Pro Arg Thr Ser Gln Phe Thr Lys Tyr Trp Thr Glu Ser
385             390                 395                 400

Asn Gly Val Glu Ser Lys Ser Leu Thr Pro Ala Leu Cys Arg Thr Pro
            405                 410                 415

Ala Asn Lys Leu Lys Asn Lys Glu Asn Val Tyr Thr Pro Lys Ser Ala
            420                 425                 430

Val Lys Asn Glu Glu Tyr Phe Met Phe Pro Glu Pro Lys Thr Pro Val
            435                 440                 445

Asn Lys Asn Gln His Lys Arg Glu Ile Leu Thr Thr Pro Asn Arg Tyr
            450                 455                 460

Thr Thr Pro Ser Lys Ala Arg Asn Gln Cys Leu Lys Glu Thr Pro Ile
465             470                 475                 480

Lys Ile Pro Val Asn Ser Thr Gly Thr Asp Lys Leu Met Thr Gly Val
            485                 490                 495

Ile Ser Pro Glu Arg Arg Cys Arg Ser Val Glu Leu Asp Leu Asn Gln
            500                 505                 510

Ala His Met Glu Glu Thr Pro Lys Arg Lys Gly Ala Lys Val Phe Gly
            515                 520                 525

Ser Leu Glu Arg Gly Leu Asp Lys Val Ile Thr Val Leu Thr Arg Ser
            530                 535                 540

Lys Arg Lys Gly Ser Ala Arg Asp Gly Pro Arg Arg Leu Lys Leu His
545             550                 555                 560

Tyr Asn Val Thr Thr Thr Arg Leu Val Asn Pro Asp Gln Leu Leu Asn
            565                 570                 575

Glu Ile Met Ser Ile Leu Pro Lys Lys His Val Asp Phe Val Gln Lys
            580                 585                 590

Gly Tyr Thr Leu Lys Cys Gln Thr Gln Ser Asp Phe Gly Lys Val Thr
            595                 600                 605

Met Gln Phe Glu Leu Glu Val Cys Gln Leu Gln Lys Pro Asp Val Val
            610                 615                 620

Gly Ile Arg Arg Gln Arg Leu Lys Gly Asp Ala Trp Val Tyr Lys Arg
625             630                 635                 640

Leu Val Glu Asp Ile Leu Ser Ser Cys Lys Val
            645                 650
```